United States Patent [19]
Roufogalis et al.

[11] Patent Number: 5,859,067
[45] Date of Patent: Jan. 12, 1999

[54] USE OF NATURAL PRODUCTS AND RELATED SYNTHETIC COMPOUNDS FOR THE TREATMENT OF CARDIOVASCULAR DISEASE

[76] Inventors: Basil Don Roufogalis, 40 Pymble Ave., Pymble, NSW 2073; Colin Charles Duke, 19 Titania St., Randwick, NSW 2031; Qian Li, 1/3 Carrington St., Lewisham, NSW 2049, all of Australia

[21] Appl. No.: 969,145

[22] Filed: Nov. 12, 1997

Related U.S. Application Data

[62] Division of Ser. No. 553,714, filed as PCT/AU94/00297 Jun. 3, 1994.

[30] Foreign Application Priority Data

Jun. 3, 1993 [AU] Australia ................................. PL9181

[51] Int. Cl.$^6$ ............................ A61K 31/05; C07C 39/14
[52] U.S. Cl. ............................................ 514/732; 568/735
[58] Field of Search ..................................... 514/457, 732; 549/399; 568/735

[56] References Cited

U.S. PATENT DOCUMENTS 4,716,252  12/1987  Wagner et al. .......................... 568/729

OTHER PUBLICATIONS

Biochem. Soc. Trans., vol. 20, No. 3, 1992, 249S, M. Wictome et al., "Mechanism of action of $Ca^{2+}$–ATPase inhibitors"—entire document.

Biochem. Med. Metal. Biol., 45,2,209–215 (1991), Teo Tian–Seng et al., "Does Calmodulin Mediate Inhibition of Human Erythrocyte $Ca^{2+}$–Pumping ATPase by Myricetin"—entire document.

Biochem.J. (1991)273, 489–492, F.B. Davis et al., "Sex–dependent inhibition by retinoic acid of thyroid–hormone action on rabbit reticulocyte $Ca^{2+}$–ATPase activity"—entire document.

J. Biol. Chem., vol. 265, No. 19, 5 Jul. 1990, 10993–9, T. Kawashima et al., "Selective Inhibition by Lasalocid of Hydrolysis of the ADP–insensitive Phosphoenzyme in the Catalytic cycle of Sarcoplasmic Reticulum. $Ca^{2+}$–ATPase"—entire document.

Biochemistry, vol. 29, No. 12, 1990, 3091–3101, F. Michelangeli et al., Mechanism of Inhibition of the ($Ca^{2+}$–$Mg^{2+}$)–ATPase by Nonylphenol—entire document.

Biochem. Pharmacology,. vol. 39, No. 4, 769–774, 1990, G. Vile et al., "Thiol Oxidation and Inhibition of Ca–ATPase by Adriamycin in Rabbit Heart Microsomes"—entire document.

J. Biol. Chem. vol. 264, No. 34, 5 Dec. 1989, 20339–43, J.H. Petretski et al., "Activation of $Ca^{2+}$ Uptake and Inhibition of Reversal of The Sacroplasmic Reticulum $Ca^{2+}$ Pump by Aromatic Compounds" entire document.

Contraception, vol. 39, No. 4, Apr. 1989, 431–45, U. Kanwar et al, "Gossypol inhibition of $Ca^{++}$ uptake and $Ca^{++}$–ATPase in human ejaculated Spermatozoal plasma membrane vesticles"—entire document.

Biochemical Pharmacology, vol. 40, No. 8, 1990, 1877–1884, J.O. Malva et al., Action of Antiestrogens on The ($Ca^{2+}$+$Mg^{2+}$)–ATPase and $Na^+/Ca^{2+}$ exchange of brain contex membranes—entire document.

Chemical Abstracts, vol. 116, 1992, Abstract 148483u, Otsuka Pharmaceutical Factory, Inc., "Flavanone derivatives from Sophora leachiana" (&JP 3246291)—abstract.

Aust. J. Chem., 1968, 21,2989–99, M. Rasmussen et la., "Chemical Studies of the Proteaceae III".—formula (Ia) p. 2989.

Aust. J. Chem., 1970,23,147–83, D.D. Ridley et al., "Chemical studies of the Proteaceae IV". formulae (1)–(3) and (5)–(6) p. 148, p. 172 lines 23–35.

M. Windholz, Ed, The Merck Index, 10th Ed, published 1983 by Merck & Co, Inc. (Rahway, N.J.) especially monographs 39,1883, 2233, 2802, 3056, 3085, 3428, 4216, 4593, 5065, 5291, 5774, 6235, 7115 and 8056 especially Monographs 23, 863, 952, 1730, 2217, 2546, 2869, 3075, 3567, 3755, 3815, 5928, 7215 8164 and 8897.

Chem. Pharm. Bull, 34,5, 1986, 2094–2099, T. Ohmoto et al., "Inhibition of Adenosine 3',5'–cycle Monophosphate Phosphodiesterase by Componenets of Sophora flavescens Aiton". Kushenol A, Table I p. 2096.

(List continued on next page.)

*Primary Examiner*—Alan L. Rotman
*Assistant Examiner*—Charanjit S. Aulakh
*Attorney, Agent, or Firm*—Kelly Bauersfeld Lowry & Kelley, LLP

[57] ABSTRACT

Use of a compound of formula (I), wherein Ar is an aromatic ring system comprising one or more optionally substituted phenyl rings optionally linked to or fused with one or more other optionally substituted phenyl rings or one or more 5 or 6–membered, optionally substituted heterocyclic rings wherein the heteroatom is oxygen; and wherein the ring system comprises 1–4 phenyl rings and wherein Ar can be linked to another Ar via a group X wherein the Ar is independently selected; where X is optionally substituted $C_{1-20}$alkylene, $C_{2-20}$alkenylene or $C_{2-20}$alkynylene; R is hydrogen; $C_{1-20}$alkenyl, $C_{2-20}$alkynyl, $C_{2-20}$alkanoyl, $C_{2-20}$alkynoyl, each of which can be optionally substituted; $R_1$ is independently selected and is hydrogen; optionally substituted $C_{1-12}$alkyl, $C_{2-12}$alkenyl, $C_{2-12}$alkynyl; —COOR'—NR'R', halogen, —OR', —COR', —CONR'R', =O, —SR', —$SO_3$R', —$SO_2$NR'R', —SOR', —$SO_2$R', —$NO_2$, —CN, glycoside, silyl; where R' is independently hyrogen; alkyl, alkenyl or akynyl each optionally substituted; and where two groups $R_1$ can be joined; wherein the optional substituents are one or more independently selected from $C_{1-10}$alkyl, $C_{2-10}$alkenyl, $C_{2-10}$alkynyl; —COOR"—NR"R", halogen, OR", —COR", —CONR"R", —SR", =O, —$SO_3$R", —$SO_2$NR"R", —SOR", —$SO_2$", —$NO_2$, —CN; wherein R" is independently hydrogen, alkyl, alkenyl, or alkynyl; n=1, 2 or 3; m=1, 2, 3 or 4; or a pharmaceutically acceptable derivative thereof in the manufacture of a medicament for inhibiting the action of $Ca^{2+}$-ATPase enzymes. Certain compounds of formula (I) and 8-lavandulyl flavone pharmaceutical formulations are new.

5 Claims, 6 Drawing Sheets

OTHER PUBLICATIONS

Chem. Pharm. Bull., 37,.5, 1392–1395 (1989), T. Nikaido et al., Inhibition of Adenosine 3',5'–Eyclic Monophosphate Phospholiesterase by Flavonoids. III Compount 48, Table I p. 1393.

Phytochemistry, vol. 31, 1992, 999–1001, N. Ruangruagsi et al., "Three flavanones with a lavandulyl group in The roots of Sophora Exigua". entire document.

Phytochemistry, vol. 33, No. 1, 1993, 203–8, M. Iinuma et al., "Seven phenolic compounds in The roots of Sophora Exigua". entire document.

Physiological Reviews, vol. 71, No. 1, Jan. 1991, 129–153, E. Carafoli; "Calcium pump of the plasma membrane" p. 134 col. 2 lines 44–45 Quercetin entire document.

US,A, 2321620 (B.C. Pratt) 15 Jun. 1943 Example II, p. 2 col. 2 lines 59–73.

"Activation of $Ca^{2+}$ Release from Sarcoplasmic Reticulum Vesicles by 4–Alkylphenols" by Troy James Beeler and Kenneth S. Gable. Archives of Biochemistry and Biophysics, vol. 301, No. 2, Mar., pp. 216–220, 1993.

"Modulation of the Activities of Membrane Enzymes by Cereal Grain Resorcinolic Lipids", Z. Naturforsch. 47c, 41–46 (1992); received Oct. 18, 1990/Apr. 16, 1991, by Arkadiusz Kozubek, Malgorzata Nietubyc, and Aleksander F. Sikorski.

"Modification of ATP regulatory function in sarcoplasmic reticulum $Ca^{2+}$–ATPase by hydrophobic molcules", by Herman Wolosker, Jorge H. Petreski and Leopoldo De Meis, Eur. J. Biochem. 193, 873–877–(1990).

"Effects of Cannabinoids on Cardiac Mocrosomal CaAtPase Activity and Calcium Uptake" by Fred G. Collins and Coryce O. Haavik Chemical Pharmacology, vol. 28, pp. 23–3–2306. 1979.

"Effect of Diethylstilbestrol and Related Compounds on the $Ca^{2+}$–Transporting ATPase of Sarcoplasmic Reticulum", Nov. 22, 1991 By Francisco Martinez–Azorin, Jose A. Teruel, Francisco Fernandez–Belda, and Juan C. Gomez–Fernandez, pp. 11923–11929.

"Characterisation of a novel $Ca^{2+}$ pump inhibitor (bis–phenol) and its effects on intracellular $Ca^{2+}$ mobilization", Biochimica et Biophysica Acta 1195 (1994) 252–258, by Graham R. Brown, et al., Received 22 Feb. 1994.

"Plant Antimutagenic Agents, 4. [1]Isolation and Structure Elucidation of Maesol. An Inactive Constituent of Maesa SPP." by Monroe E. Wall, et al., Journal of Natural Products, vol. 51. No. 6, pp. 1226–1231, Nov.–Dec. 1988.

USE OF NATURAL PRODUCTS AND RELATED SYNTHETIC COMPOUNDS FOR THE TREATMENT OF CARDIOVASCULAR DISEASE

This is a division, of application Ser. No. 08/553,714, filed as PCT/AU94/00297, Jun. 3, 1994.

TECHNICAL FIELD

The present invention relates to the use of naturally occurring phenolic compounds and related synthetic compounds in the treatment or prophylaxis of cardiovascular disease and to novel phenolic compounds and the use thereof in the treatment or prophylaxis of cardiovascular disease.

BACKGROUND ART

Cardiovascular disease is a serious health problem and a major cause of death in Australia and most developed countries. It has been reported that calcium is central to cardiovascular function, in that the calcium ion controls the contraction of heart muscle and the tone of blood vessels. Certain drugs have been used to increase intracellular calcium in order to stimulate the failing heart (cardiotonic agents). The major drugs used for congestive heart failure in the past are derived from digitalis, found naturally in plants such as foxglove. Their action to raise intracellular calcium, however, is indirect, as they inhibit $Na^+,K^+$-ATPase which results in an increase in intracellular $Na^+$, which then in turn stimulates the inflow of extracellular calcium and in turn stimulates the failing heart. These drugs are not ideal as they are toxic at doses only slightly higher than therapeutic cardiotonic concentrations. There has been an active search for alternative cardiotonic agents in recent years and there is still a need for effective drugs to treat and prevent various aspects of cardiovascular disease.

$Ca^{2+}$ has a variety of functions in most animal cells. The concentration of free calcium ion ($Ca^{2+}$) in the cytoplasmic space acts as an intracellular messenger in both electrical and non-electrical excitable cells. The important role of $Ca^{2+}$ is in relation to cellular contraction, and proliferation especially contraction and relaxation of the heart.

The movement of $Ca^{2+}$ across cells is regulated by number of mechanisms. If there are means that can pharmacologically manipulate these processes then the level of free intracellular $Ca^{2+}$ may be altered, resulting in a change in cellular response.

There are number of calcium pools which contribute to the concentration of $Ca^{2+}$ in the cytoplasmic space. Two major important pools are namely, the extracellular pool and the internal store, the so-called sarcoplasmic reticulum (SR) store.

The entry of extracellular $Ca^{2+}$, down its electrochemical gradient, not only raises the level of intracellular $Ca^{2+}$ but also initiates the release of $Ca^{2+}$ from the SR store. This phenomenon explains the rapid contraction of cells. The rise of intracellular $Ca^{2+}$ is compensated by a number of mechanisms to remove $Ca^{2+}$ from the cytoplasmic space, either by extruding the $Ca^{2+}$ out of the cell through the $Ca^{2+}$ pump, which is biochemically coupled to $Ca^{2+}$-ATPase, and the $Ca^{2+}/Na^+$ exchanger, and by sequestering of $Ca^{2+}$ back into the SR store through SR $Ca^{2+}$-ATPase. These removal mechanisms are energy-dependent processes that utilise ATP as the energy source.

The present inventors have found that a range of naturally occurring phenols and related synthetic compounds manipulate the plasma membrane $Ca^{2+}$-ATPase process named, hereafter, as the plasma membrane $Ca^{2+}$-ATPase. It is anticipated that they may also alter the SR $Ca^{2+}$-ATPase, given the similarity of this enzyme to this plasma membrane $Ca^{2+}$-ATPase. Compounds discovered can inhibit the plasma membrane $Ca^{2+}$-ATPase causing an increased level of free $Ca^{2+}$ inside cell. At the same time, some of the compounds may be chosen to stimulate the SR $Ca^{2+}$-ATPase, thereby increasing $Ca^{2+}$ uptake into the internal SR store and making more $Ca^{2+}$ available for release from the SR. The overall effect of these compounds is to increase the rate of contraction as well as the force of contraction of the heart cells, and particular of the failing heart.

It has been reported that a number of nonspecific reagents inhibit plasma membrane $Ca^{2+}$-ATPase. It has also been reported that a number of long chain alcohols, hemin and nonhemin iron and fatty acids partially inhibit $Ca^{2+}$-ATPase of erythrocyte membrane. The retinoids have been shown to have anti-calmodulin effects and therefore indirect effects on the $Ca^{2+}$-pump enzyme. The sesquiterpene lactone thapsigargin was found to be a specific inhibitor of $Ca^{2+}$-ATPase of skeletal muscle endoplasmic reticulum.

DISCLOSURE OF THE INVENTION

In one aspect, the present invention provides the use of a compound of formula (I), a pharmaceutically acceptable salt or ester thereof in the inhibition of $Ca^{2+}$-ATPase enzymes

wherein Ar is an aromatic ring system comprising one or more optionally substituted phenyl rings optionally linked to or fused with one or more other optionally substituted phenyl rings or one or more 5 or 6-membered, optionally substituted heterocyclic rings wherein the heteroatom is oxygen; and wherein the ring system comprises 1–4 phenyl rings and wherein Ar can be linked to another Ar via a group X wherein the Ar is independently selected;

where X is optionally substituted $C_{1-20}$alkylene, $C_{2-20}$alkenylene or $C_{2-20}$alkynylene;

R is hydrogen; $C_{1-20}$alkyl, $C_{2-20}$alkenyl, $C_{2-20}$alkynyl, $C_{2-20}$alkanoyl, $C_{2-20}$alkenoyl, $C_{2-20}$alkynoyl, each of which can be optionally substituted;

$R_1$ is independently selected and is hydrogen; optionally substituted $C_{1-12}$alkyl, $C_{2-12}$alkenyl, $C_{2-12}$alkynyl; —COOR'—NR'R', halogen, —OR', —COR', —CONR'R', =O, —SR', —SO$_3$R', —SO$_2$NR'R', —SOR', SO$_2$R', —NO$_2$, —CN, glycoside, silyl;

where R' is independently hydrogen; alkyl, alkenyl or alkynyl each optionally substituted; and where two groups $R_1$ can be joined;

wherein the optional substituents are one or more independently selected from $C_{1-10}$alkyl, $C_{2-10}$alkenyl, $C_{2-10}$ alkynyl; —COOR"—NR"R", halogen, —OR", —COR", —CONR"R", —SR", =O, —SO$_3$R", —SO$_2$NR"R", —SOR", —SO$_2$R", —NO$_2$, —CN; wherein R" is independently hydrogen, alkyl, alkenyl, or alkynyl;

n=1, 2 or 3 m=1, 2, 3 or 4.

Preferably, the use of compounds of formula (I) is in the inhibition of plasma membrane $Ca^{2+}$-ATPase.

In a second aspect, the present invention provides the use of a compound of formula (I), a pharmaceutically acceptable salt or ester thereof in the treatment or prophylaxis of cardiovascular disease.

In a third aspect, the present invention provides novel compounds of formulae (II), (III), (IV), (V), (VI) or pharmaceutically acceptable derivatives thereof:

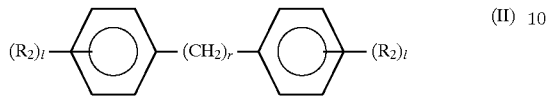
(II)

where
$l=1, 2$ or $3$
$r=7-14$ when $l=1$ $8-16$ when $l=2$ or $3$
$R_2$ is (1) 2-hydroxy
   (2) 2-hydroxy-4'-hydroxy
   (3) 2-hydroxy-3-methyl
   (4) 4-hydroxy-3-methyl
   (5) 2,4-dihydroxy
   (6) 3,5-dihydroxy-4-methyl
   (7) 2,6-dihydroxy-4-methyl
   (8) 2,4-dihydroxy-3-methyl
   (9) 3-hydroxy-4-methyl provided that (1) when $R_2$ is 2-hydroxy and $l=1$ then $r$ is not 7–10 and
   (2) when $l=3$ and $R_2$ is 3,5-dihydroxy-4-methyl then n is not 14 and
   (3) when $l=2$ and $R_2$ is 2-hydroxy-3-methyl then n is not 10
   (4) when $l=2$ and $R_2$ is 2,4-dihydroxy then $r$ is not 8–10 and 13 and
   (5) when $l=2$ and $R_2$ is 4-hydroxy-3-methyl then $r$ is not 10;

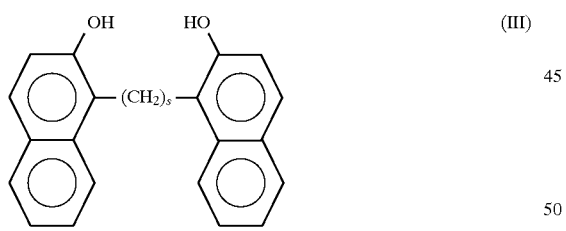
(III)

where $s=8-16$

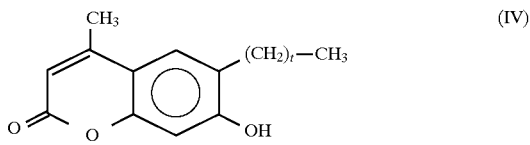
(IV)

where $t=6-15$

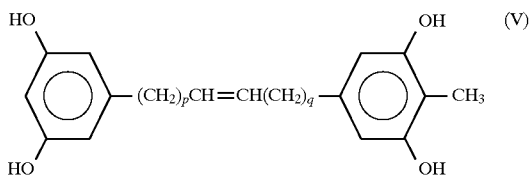
(V)

where $p+q=12$

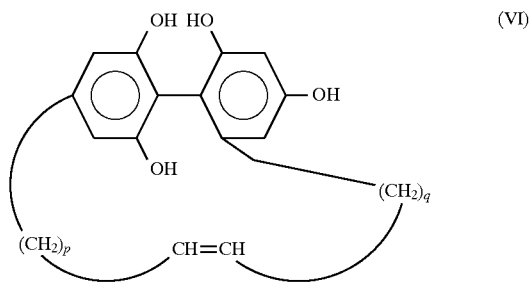
(VI)

where $p+q=12$

In a fourth aspect, the present invention provides a method of preparing compounds of formula (II) which comprises
   (a) where $l=1$ and $R_2$ is OH
      (i) treating the corresponding diacid with a suitable agent to provide the acid dichloride as follows
      $HOOC—(CH_2)_{r-2}—COOH \rightarrow ClOC—(CH_2)_{r-2}—COCl$
      (ii) treating the corresponding acid dichloride with phenol as follows
      $ClOC—(CH_2)_{r-2}—COCl + PhOH \rightarrow PhOCO—(CH_2)_{r-2}—COOPh$
      (iii) rearrangement of the diacyl groups as follows

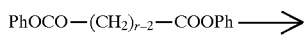 

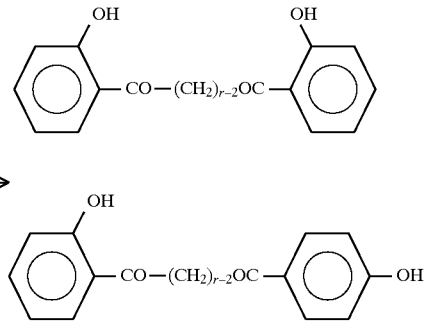

(iv) followed by reduction of the acyl groups to provide compounds of formula (II);

(b) where l=2, R$_2$ is OH
  (i) treating the corresponding diacid with zinc chloride and resorcinol; and
  (ii) followed by reduction of the acyl groups to provide compounds of formula (II);

(c) where l=2, R$_2$ is 2-hydroxy-3-methyl carrying out steps (i)–(iv) in (a) above except in (ii) phenol is replaced with o-cresol;

(d) where l=2 and R$_2$ is 3-hydroxy-4-methyl
  (i) nitrating the corresponding diketo compound of formula

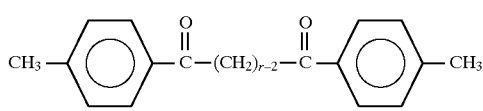

to give the corresponding bis-3-nitro compound
  (ii) reducing the bis-3-nitro compound to give the bis-3-amino compound followed by
  (iii) diazotisation and hydrolysis to give the bis-3-hydroxy compound
  (iv) followed by reduction of the keto groups to give the desired bis-3-hydroxy compound;

(e) where l=3 and R$_2$ is 2,6-dihydroxy-4-methyl
  (i) treatment of a compound of formula

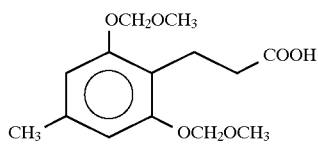

with LDA to give the dianion followed by
  (ii) treatment with the desired protected alkane aldehyde of formula

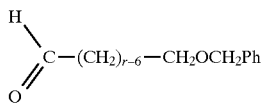

to give

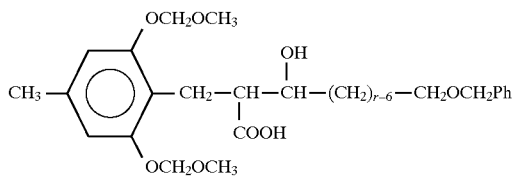

(iii) dehydrative decarboxylation followed by reduction to give an intermediate product of formula

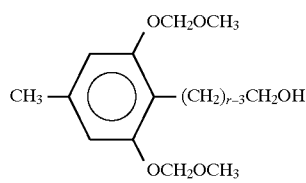

(iv) oxidation to give

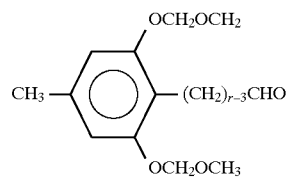

(v) followed by treatment with the dianion from step (i) to give

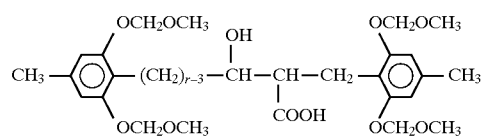

(vi) dehydrative decarboxylation followed by deprotection and reduction to give the desired product;

(f) where l=3 and R$_2$ is 3,5-dihydroxy-4-methyl
  (i) treatment of α-N,N-dimethylamino-α-cyano-(3,5-dimethoxy-4-methyl)benzylidene in tetrahydrofuran and hexamethylphosphoramide (HMPA) with lithium diisopropylamide (LDA) to give the anion followed by
  (ii) treatment with α,ω-dibromoalkanes to give

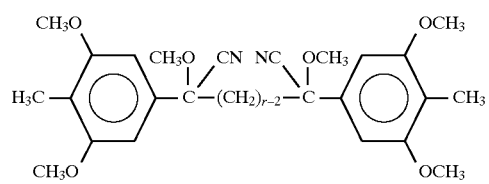

(iii) refluxing with 30% aqueous oxalic acid to give the corresponding diacyl compound
  (iv) reduction of the acyl groups
  (v) followed by demethylation with hydrogen bromide in acetic acid to provide compounds of formula (II);

(g) where l=3 and R$_2$ is 2,4-dihydroxy-3-methyl
  (i) carrying out steps (i) and (ii) in (b) except in (i) resorcinol is replaced with 2-methylresorcinol;

(h) where l=2 and R$_2$ is 4-hydroxy-3-methyl
  (i) treating the corresponding diacid with ortho-cresol in the presence of polyphosphoric acid to give the corresponding diacyl compound
  (ii) followed by reduction the acyl groups to provide compounds of formula (II).

In a fifth aspect, the present invention provides a method of preparing compounds of formula (III) which comprises
  (i) treating the corresponding diacid with a suitable agent to provide the acid dichloride
  (ii) treating the corresponding acid dichloride with 2-naphthol followed by
  (iii) rearrangement of the diacyl groups and
  (iv) followed by reduction of the acyl groups to provide compounds of formula (III)

In a sixth aspect, the present invention provides a method of preparing compounds of formula (IV) which comprises treatment of 4-alkylresorcinols with ethyl acetoacetate in the presence of an acid catalyst to give compounds of formula (IV).

Preferably, Ar is phenyl, naphthalene, anthracene, naphthacene or phenanthrene. More preferably, Ar is phenyl.

All alkyl, alkenyl or alkynyl carbon chains can be straight or branched chain.

Halogen includes bromo, chloro, fluoro or iodo.

The 5 or 6-membered heterocyclic ring can be saturated, partially unsaturated or unsaturated.

Pharmaceutically acceptable derivatives include pharmaceutically acceptable ethers, esters and acid addition salts.

In the preparation of compounds of formula (II), preferably, the acid dichloride is formed by treating the corresponding diacid with thionyl chloride. However, any other suitable agent can be used.

Preferably, in the preparation of compounds of formula (IV) the acid catalyst is boron trifluoride etherate or the like.

Preferably, the rearrangement of the acyl groups to the required positions on the phenyl ring is carried out using $CS_2$ and $AlCl_3$ as catalyst. The catalyst can generally be any Lewis acid such as $BF_3$, $ZnCl_2$, $FeBr_3$ or the like.

The reduction of the acyl group is preferably carried out using amalgamated zinc and a mixture of hydrochloric acid and optionally acetic acid.

Nitration is preferably carried out in the usual way using a combination of nitric acid and sulfuric acid ($HNO_3$/$H_2SO_4$). The reduction of the nitrate to the amine is preferably carried out using stannous chloride and hydrochloric acid ($SnCl_2$/HCl).

Diazotisation is preferably carried out by treatment with aq. $H_2SO_4$/$NaNO_2$ and hydrolysis is usually carried by using 10% $H_2SO_4$.

Dehydrative decarboxylation is preferably carried out by using N-ethoxycarbonyl-2-ethoxy-1,2-dihydro-quinoline and deprotection by using p-TsOH/MeOH.

In another aspect, the present invention provides the use of a compound of formula (I) or a pharmaceutically acceptable derivative thereof in the manufacture of a medicament for inhibition of $Ca^{2+}$-ATPase enzymes, preferably, plasma membrane $Ca^{2+}$-ATPase.

In yet another aspect, the present invention provides the use of a compound of formula (I) or a pharmaceutically acceptable derivative thereof in the manufacture of a medicament for the treatment or prophylaxis of cardiovascular disease.

Figure 1:
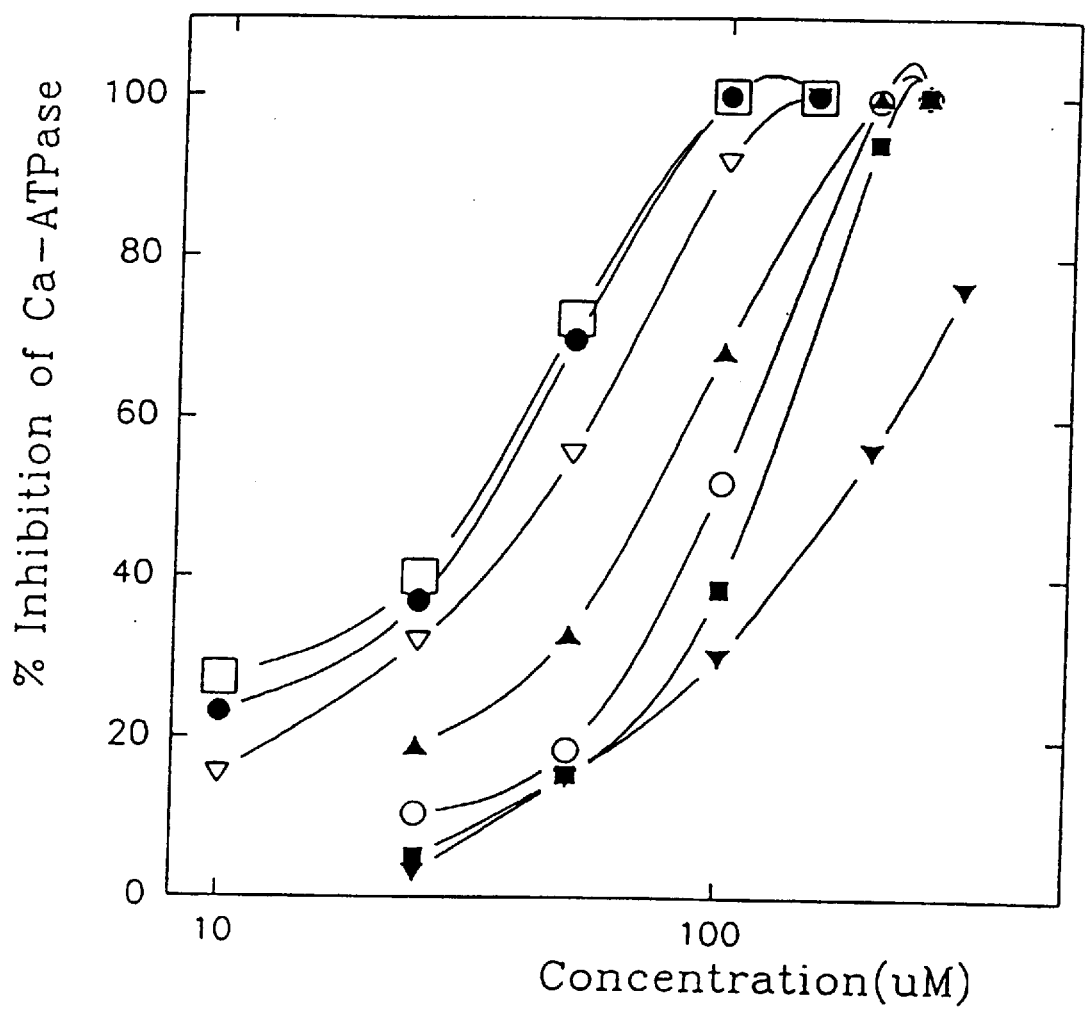
FIG. 1 is a graph showing concentration dependency of inhibition of erythrocyte plasma membrane of synthetic alkyl phenols.
Figure 2:
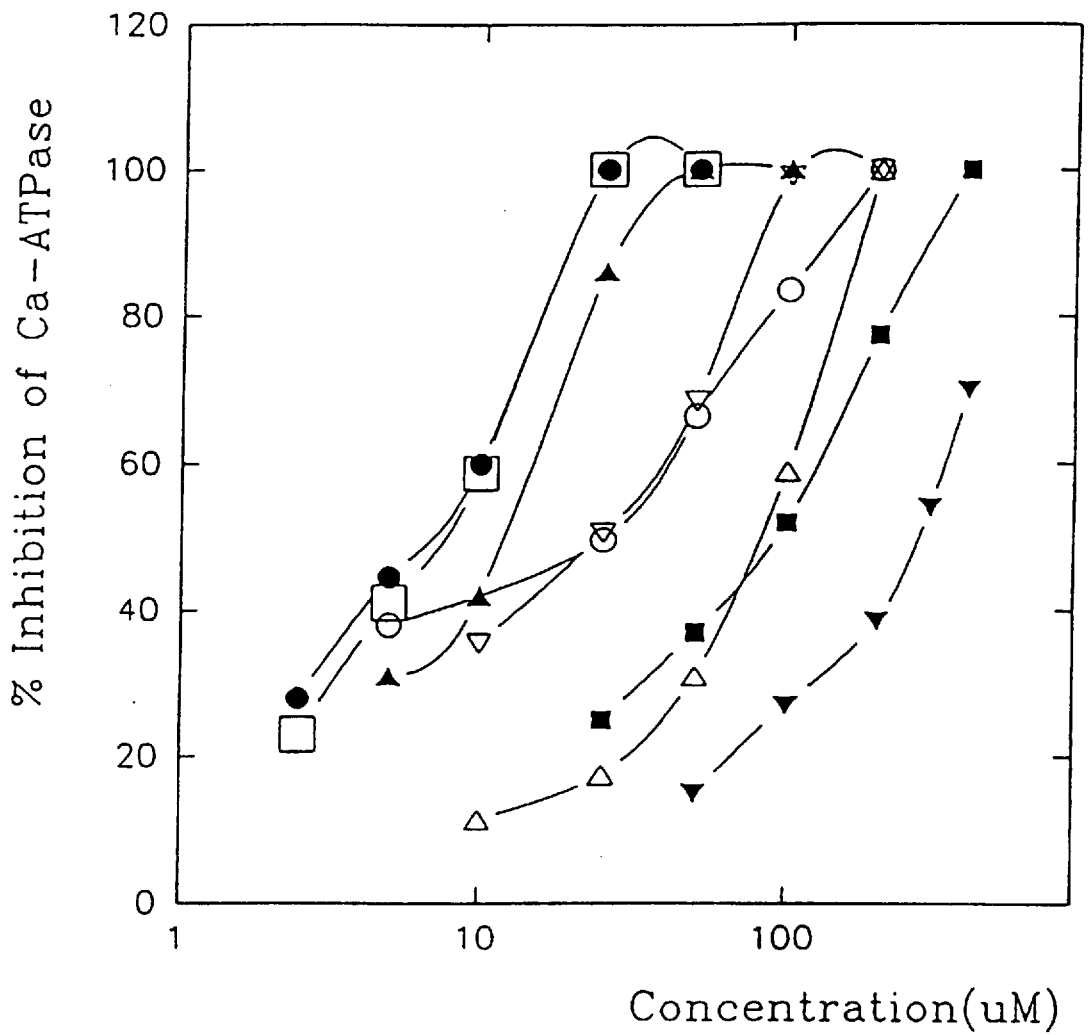
Figure 3:
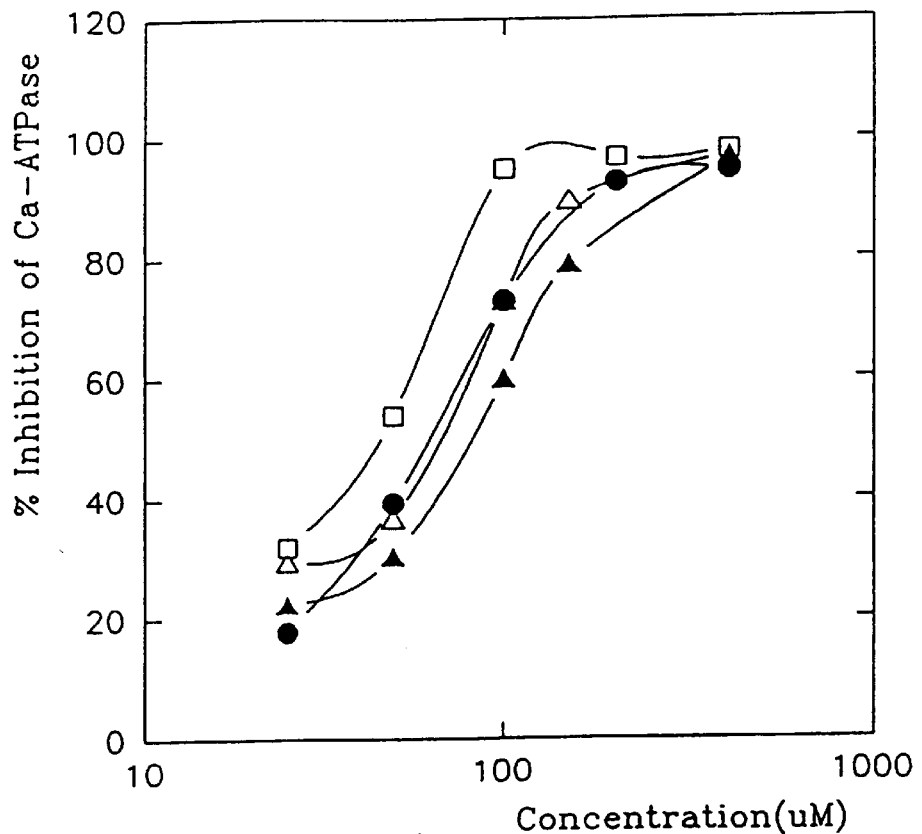
Figure 4:
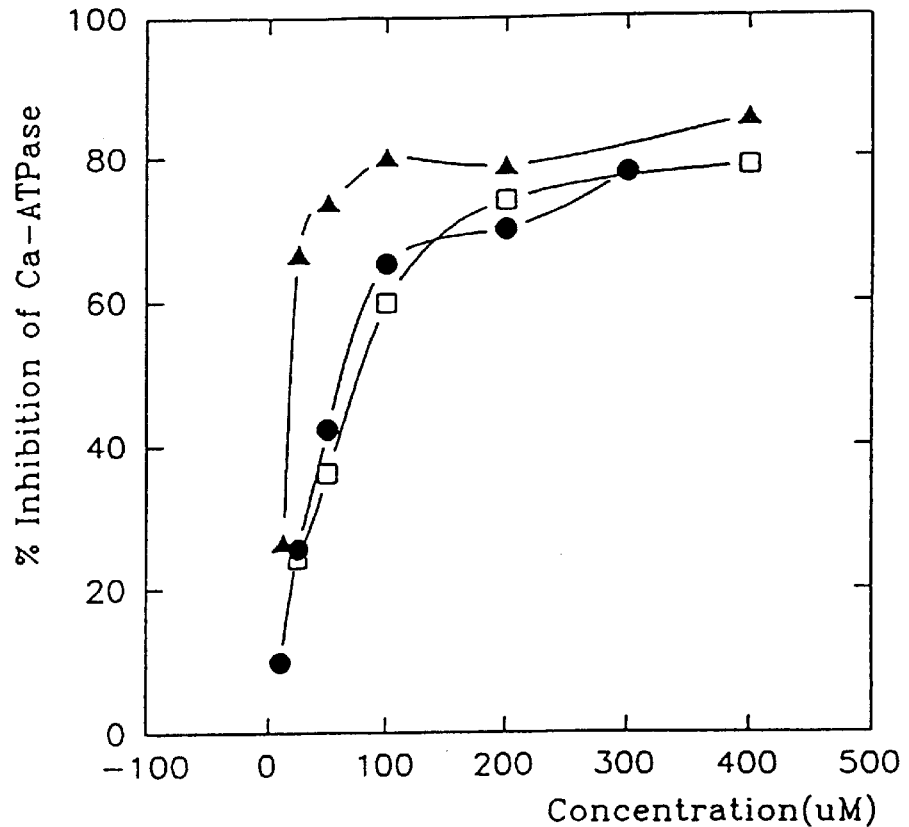
Figure 5:
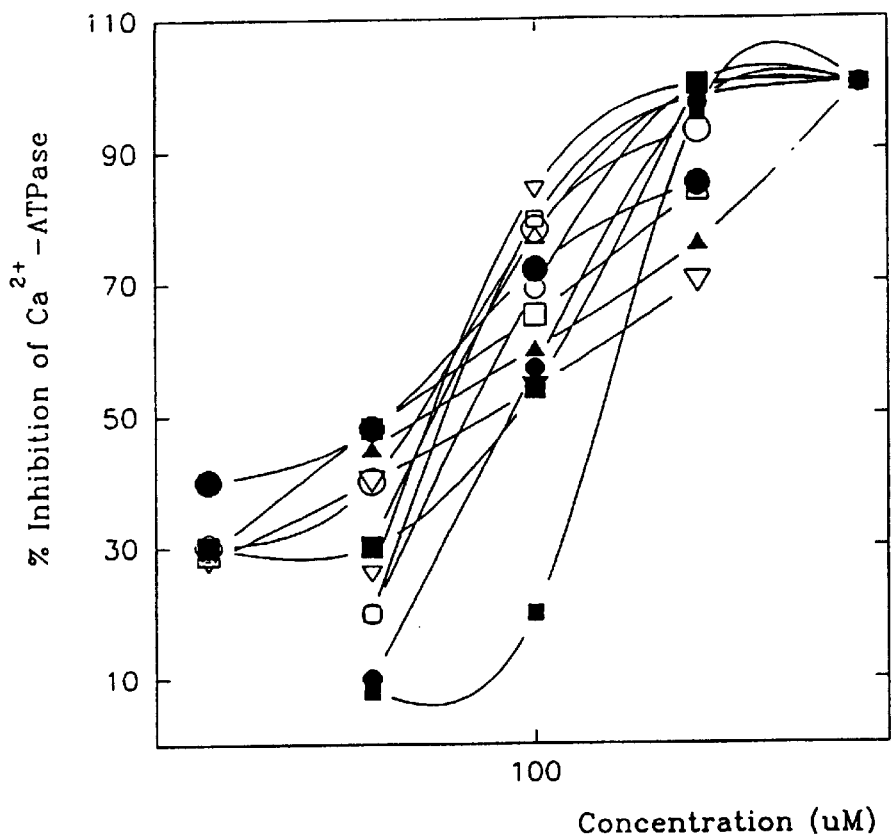
Figure 6:
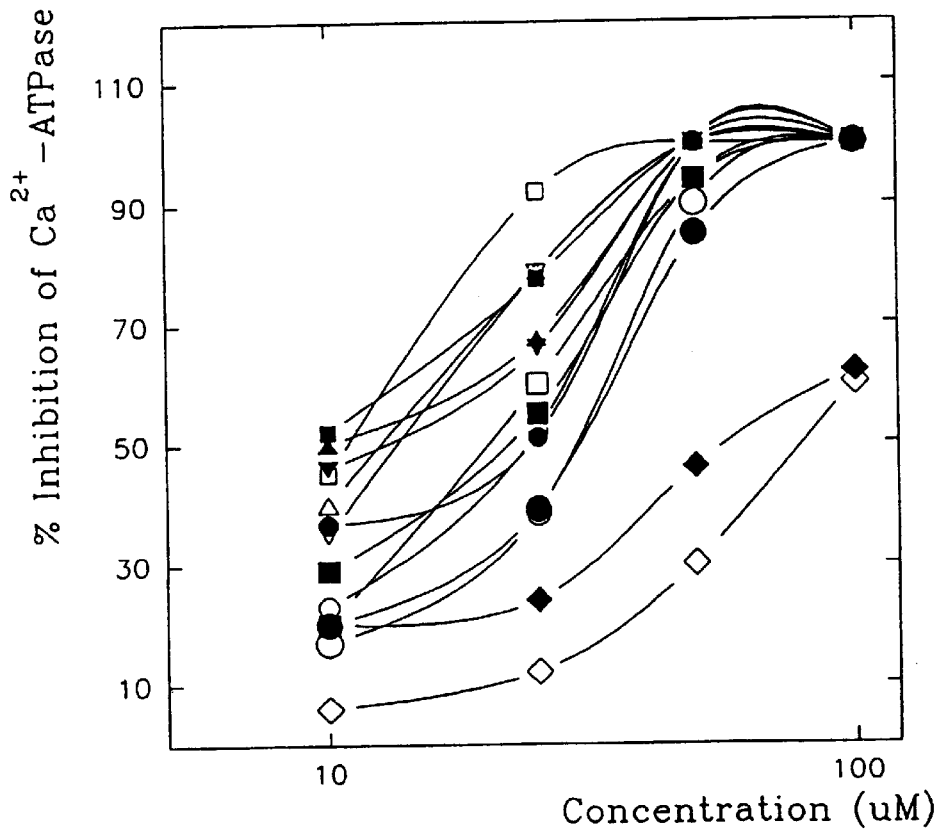

FIG. 2 is a graph showing concentration dependency of inhibition of erythrocyte plasma membrane of synthetic bis(hydroxyphenyl)alkanes.
- ● 1,10-bis(2-hydroxyphenyl)decane
- □ 1,12-bis(2-hydroxyphenyl)dodecane
- ○ 1,14-bis(2-hydroxyphenyl)tetradecane
- ▼ 1-(2-hydroxyphenyl)-10-(4-hydroxyphenyl)decane
- ▽ 1-(2-hydroxyphenyl)-12-(4-hydroxyphenyl)dodecane
- △ 1-(2-hydroxyphenyl)-14-(4-hydroxyphenyl) tetradecane
- ■ 1,10-bis(4-hydroxyphenyl)decane
- ▼ 1,14-bis(4-hydroxyphenyl)tetradecane FIG. 3 is a graph showing concentration dependency of inhibition of erythrocyte plasma membrane of resorcinol derivatives.
- □ ethyl 3,5-dibromo-2,4-dihydroxy-6-nonylbenzoate
- ● ethyl 3,5-dibromo-2,4-dihydroxy-6-decylbenzoate
- △ ethyl 2,4-dihydroxy-6-nonylbenzoate
- ▲ ethyl 2,4-dihydroxy-6-decylbenzoate FIG. 4 is a graph showing concentration dependency of inhibition of erythrocyte plasma membrane of tert-butylphenols.
- ● 2,3-di-tert-butyl-4-methoxyphenol
- □ 2,6-di-tert-butylphenol
- ▲ 2,4,6-tri-tert-butylphenol FIG. 5 is a graph showing concentration dependence of $Ca^{2+}$-ATPase inhibition of 2-nonylphenol derivatives.
- ● 2-nonylphenol/○ (+CaM)
- ▼ 3-methyl-6-nonylphenol/▽ (+CaM)
- ■ 4-methyl-6-nonylphenol/□ (+CaM)
- ● 4-nitro-2-nonylphenol/○ (+CaM)
- ▽ 4-bromo-2-nitro-6-nonylphenol (+CaM)
- □ 2-bromo-4-nitro-6-nonylphenol (+CaM)
- ▲ 4-bromo-2-nonylphenol/△ (+CaM)
- ■ 4-nonylresorcinol FIG. 6 is a graph showing concentration dependence of $Ca^{2+}$-ATPase inhibition of α,ω-bis[2-hydroxy(3,4 and 5-methyl)phenyl]alkanes.
- ● 1,8-bis(2-hydroxyphenyl)octane/○ (+CaM)
- ▼ 1,9-bis(2-hydroxyphenyl)nonane/▽ (+CaM)
- ■ 1,10-bis(2-hydroxyphenyl)decane/□ (+CaM)
- ▲ 1,12-bis(2-hydroxyphenyl)dodecane/△ (+CaM)
- ◆ 1,10-bis(2-hydroxy-3-methylphenyl)decane/◇ (+CaM)
- ● 1,10-bis(2-hydroxy-4-methylphenyl)decane/○ (+CaM)
- ■ 1,10-bis(2-hydroxy-5-methylphenyl)decan/□ (+CaM)

Figure 7:
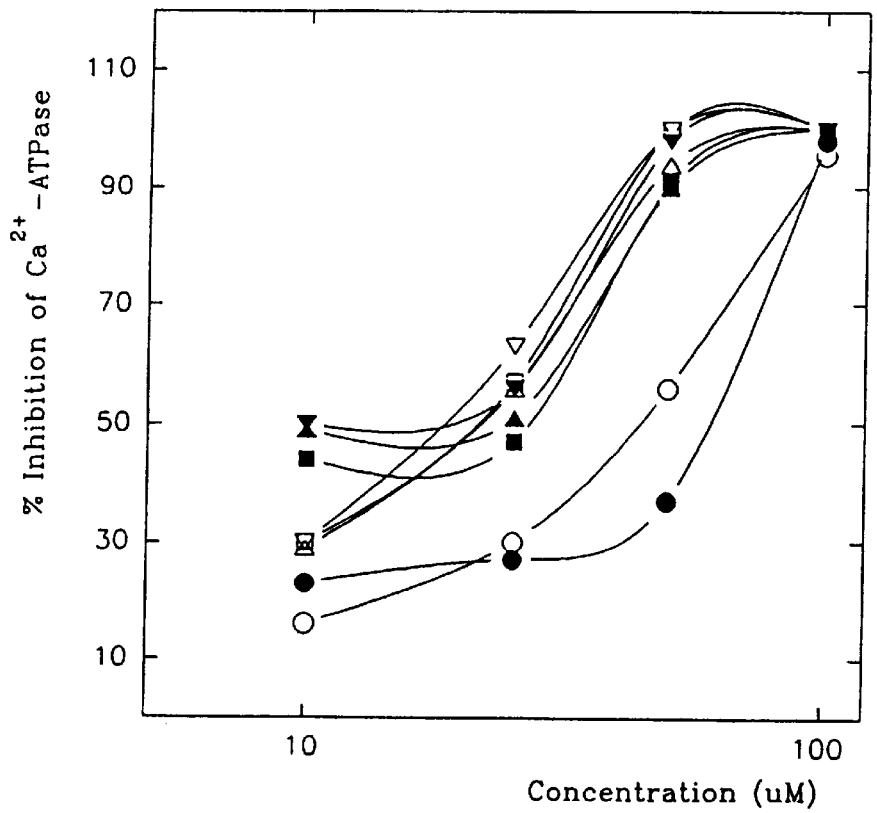

FIG. 7 is a graph showing concentration dependence of $Ca^{2+}$-ATPase inhibition of α,ω-bis[2-4-dihydroxyphenyl]alkanes.
- ● 1,8-bis(2,4-dihydroxyphenyl)octane/○ (+CaM)
- ▼ 1,10-bis(2,4-dihydroxyphenyl)decane/▽ (+CaM)
- ■ 1,11-bis(2,4-dihydroxyphenyl)undecane/□ (+CaM)
- ▲ 1,12-bis(2,4-dihydroxyphenyl)dodecane/△ (+CaM)

Figure 8:
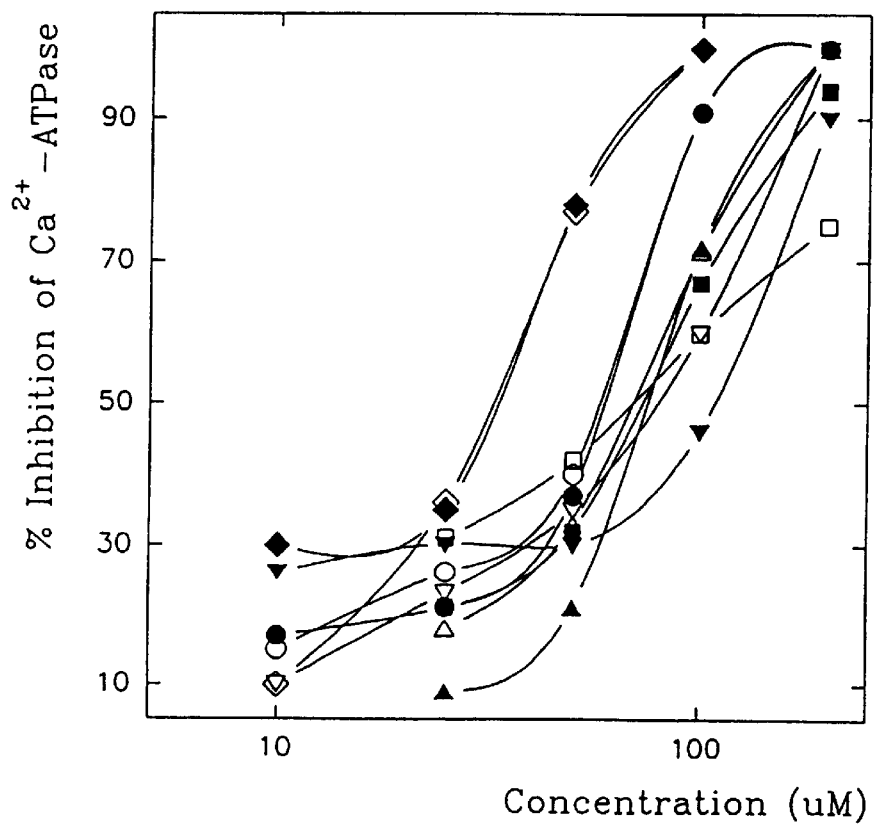

FIG. 8 is a graph showing concentration dependence of $Ca^{2+}$-ATPase inhibition of α,ω-bis[hydroxy(methyl)phenyl and naphthyl]decanes.
- ◆ 1,10-bis(3-hydroxyphenyl)decane/◇ (+CaM)
- ● 1,10-bis(3-hydroxy-4-methylphenyl)decane/○ (+Cam)
- ▼ 1,10-bis(4-hydroxy-3-methylphenyl)decane/▽ (+CaM)
- ■ 1,10-bis(2-hydroxy-1-naphthyl)decane/□ (+CaM)
- ▲ 1,1-bis(2-hydroxyphenyl)decane/△ (+CaM)

Figure 9:
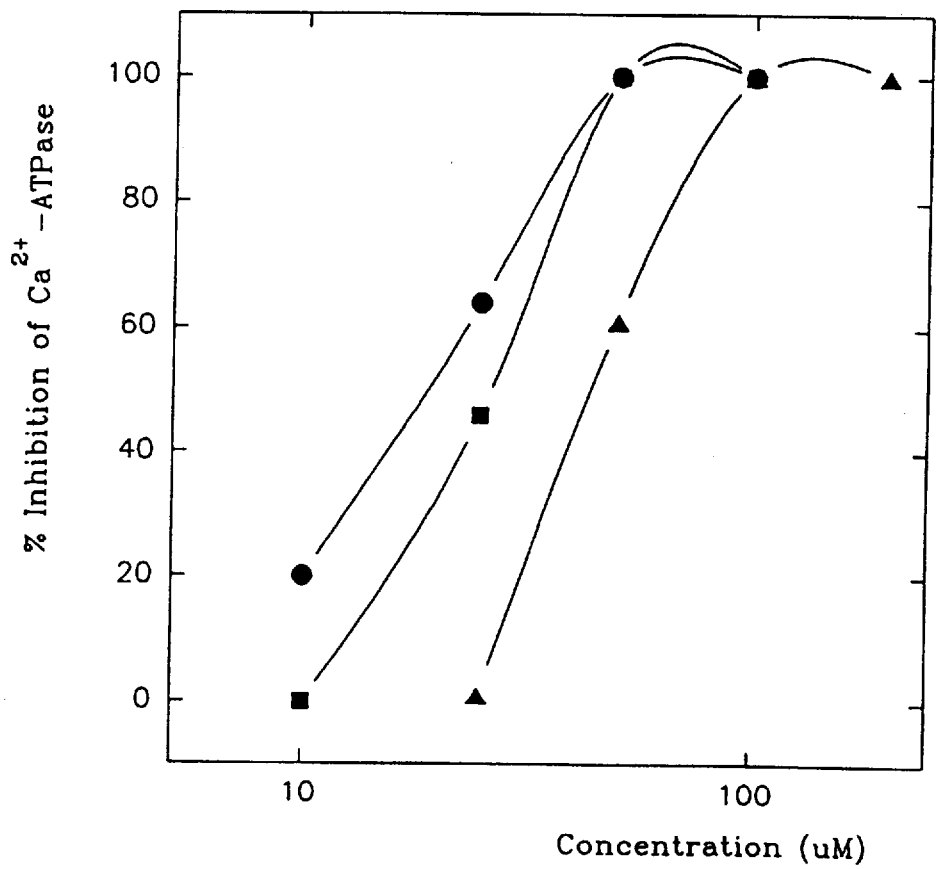

FIG. 9 is a graph showing concentration dependence of $Ca^{2+}$-ATPase inhibition of phenolic natural products.
- ● 5,7,2',6'-tetrahydroxy-8-lavandulylflavanone
- ■ 5,7,6'-trihydroxy-8-lavandulylflavanone
- ▲ 5,2',6'-trihydroxy-8-lavandulyl-7-methoxyflavanone

MODES FOR CARRYING OUT THE INVENTION

Compounds of formula (I) encompasses naturally occurring compounds as well as synthetically prepared related compounds. The naturally occurring compounds of formula (I) were extracted from endemic Australian plants of the Proteaceae family according to standard literature procedure, for example, see Ritchie E, Taylor W C and Vautin S T K (1965), Chemical studies of the Proteaceae I Aust.J.Chem., 18, 2015–2020; Rasmussen M, et al (1968) Chemical studies of the Proteaceae III. Aust.J.Chem., 21, 2989–3000 and Ridley D D, et al (1970) Chemical studies of the Proteaceae IV. Aust.J.Chem., 23 147–183.

Long-chain alkyl phenols were extracted from Grevillea and Persoonia. Novel compounds having the structural formulae (II) and (III) were extracted and isolated from *Grevillea robusta* collected in Sydney, Australia. A voucher specimen is available for inspection in the Department of Pharmacy, at the University of Sydney. Briefly, a sample of two kilograms was extracted by percolation with chloroform/ethanol (1:1) for three days. After concentration of the extract in vacuo, the residue was chromatographed using silica gel short column vacuum chromatography.

Other compounds falling within the scope of formula (I) were prepared according to literature procedures or are commercially available. Starting materials for the syntheses are commercially available or are prepared according to literature procedures.

The 2- and 4-substituted alkylphenols and α,ω-bis(hydroxyphenyl)alkanes were prepared by published methods (see E Miller and W H Hartung, Organic synthesis (1943), collective volume II, 543–545 and R R Read and J Wood, Organic syntheses (1955), collective volume III, 444–446). The syntheses were performed in three consecutive stages: firstly, the formation of the ester from an acid and phenol; secondly, the rearrangement of the acyl group, using $AlCl_3$ as catalyst, to the 2- and 4-positions relative to the hydroxy group on the phenol ring and thirdly, the reduction of the acyl group using amalgamated zinc and hydrochloric acid. The rearrangement is a time dependent reaction and generally a short reaction period provides the acyl group at the 4-position relative to the hydroxy group.

Short column vacuum chromatography was used at each stage of synthetic reactions to separate and purify the products from the reaction mixture. TLC methods were also employed to identify the products and to determine the eluent solvent required for column chromatography. The products at each stage were also characterised by NMR and CI-MS analysis.

The 3-substituted phenol derivatives were prepared according to another method, described by Itokawa H, et al (1989), A quantitative structure activity relationship for antitumor long-chain phenols from *Ginkgo biloba L.* Chem.Pharm.Bull. 37, 1619–1621. This method was used to prepare 3-nonylphenol with the aim of comparing its $Ca^{2+}$-ATPase inhibitory activity with those of the 2-and 4-substituted isomers. Hence, the importance of substitution on the phenol ring for $Ca^{2+}$-ATPase inhibition could be determined.

The bisphenol compounds were prepared, isolated and purified using procedures similar to those described above for alkylphenol, except that the preparation of esters was carried out in two separate steps.

For compounds of formula (II) where $R_2$ is 2-hydroxy-3-methyl the preparation is similar to that of the bishydroxyphenyl alkanes except instead of phenol, ortho-cresol is used following the procedure of K Kakemi et al in Antioxidants III *Yakuqaku Zasshi* 86 [9], 791–796 (1966). 3-hydroxy-4-methyl compounds of formula (II) are prepared by a similar method to that used to prepare α,ω-bis(3-hydroxyphenyl)alkanes following the procedure of K. Kakemi et al. above except that α,ω-bis(4-methylphenyl)-α,ω-alkanediones are used instead of α,ω-bisphenyl-α,ω-alkanediones. 2,4-dihydroxy compounds of formula (II) are prepared by the reaction of resorcinol with the corresponding dicarboxylic acids in the presence of zinc chloride to give the intermediate alkanediones which are then reduced.

Compounds of formula (II) where $R_2$ is 2,6-dihydroxy-4-methyl are prepared by a method similar to that used to prepare grifolin following the procedure of S Ohta et al A total synthesis of grifolin Chem.Pharm.Bull. 36 [6] 2239–2243 (1988).

The starting compound in step (e) (i) is obtained according to the procedure of S Ohta et al referred to above. The aldehyde at step (e) (ii) is obtained by alkylating commercially available compounds of formulae $X-CH_2-(CH_2)_{r-6}CH_2-OR$ where R=H, X=Cl or Br with benzyl bromide (or iodide) to give an intermediate product where $R=CH_2Ph$ followed by hydrolysis to give $HOCH_2(CH_2)_{r-6}CH_2OCH_2Ph$ followed by oxidation to give $OHC(CH_2)_{r-6}CH_2OCH_2Ph$.

Compounds of formula (II) where $R_2$ is 3,5-dihydroxy-4-methyl are prepared by a procedure similar to that described by K. Takahashi et al., J. Org. Chem. 1983, 48, 1909–1912.

Compounds of formula (II) where $R_2$ is 2,4-dihydroxy-3-methyl are prepared by a procedure similar to that described by J. von Braun et al., Ber. (1941), 74B, 1772–1783 except that 2-methylresorcinol is used instead of resorcinol.

Compounds of formula (III) are prepared by a method similar to that used to prepare α,ω-bis(2-hydroxyphenyl) alkanes following the procedure of K. Kakemi et al. Yakugaku Zasshi (1966), 86, 791–796.

Compounds of formula (IV) are prepared by a method similar to that used to prepare 6-alkyl-7-hydroxy-4-methylcoumarins following the procedure of S P Starkov, G A Goncharenko and A I Panasenko, Zh. Obshch. Khim (1993), 63 (5), 1111–1115.

Other compounds of formula (I) were prepared according to literature procedures as follows:

Bis-phenols 1,10-bis(2-hydroxyphenyl)decane and 1,10-bis(3-hydroxyphenyl)decane

Antioxidants III. K Kakemi, T Arita, R Hori, and H Takenaka *Yakuqaku Zasshi* 86 (1966) 791–796

1,10-bis(4-hydroxyphenyl)decane

α,ω-di-p-hydroxyphenyl Alkanes

E M Richardson and E E Reid *J.Am.Chem.Soc.* (1940) 62 413–415

Fries transformation of condensates of sebacic acid with phenols: 1,8-dibenzoyloctanes J P Varma and J S Aggarwal *J.Indian Chem.Soc.* (1959) 36 41–45

Synthesis of α,ω-bis(p-hydroxyalkanes)

Y E Doroshenko and V A Sergeev

*Zh. Organ. Khim.* (1965) 1 (9) 1602–1604

1,12-bis(4-hydroxyphenyl)dodecane

Synthesis of α,ω-bis(p-hydroxyalkanes)

Y E Doroshenko and V A Sergee *Zh. Organ. Khim.* (1965) 1 (9) 1602–1604

1,14-bis(4-hydroxyhenyl)tetradecane

H Goldmann et al. *J.Am.Chem.Soc.* (1988) 110 (20) 6811–6817

1,10-bis(4-hydroxy-3-methylphenyl)decane

P Schlack and W Koller Ger. 1,086,711 Aug. 11, 1960.

1,1-bis(2-hydroxyphenyl)decane

G Casiraghi et al. J. Chem. Soc. Perkin Trans 1 (1982), 3, 805–808.

Alkylphenols

The synthesis of aromatic hydroxyketones. I. ortho and para-acylphenols with normal $C_4$–$C_9$ chains.

G Sandulesco and A Girard *Bull.Soc.Chim.Fr.* (1930) 47 (4) 1300–1314

Fungicidal activity and chemical constitution,

D Wood *J.Chem.Soc.* (1955), 4391–4393

Alkylation of phenol by 1-dodecane and 1-decanol. A literature correction.

B Campbell, S Donald et al. *Bull.Chem.Soc.* Japan (1990) 63 (12) 3665–3669 decylphenol and dodecylphenol Cyclohexylphenols (ortho & para)

The direct alkylation of phenol by cyclohexene in the presence of boron trifluoride H Lejebure and E Levas *Compt. Rend.* (1945) 220 782–784 and 826–827

H Lejebure and E Levas *Compt. Rend.* (1945) 221 301–303

Syntheses of α,ω-bis(2,4-dihydroxy) compounds. Reaction of aliphatic dicarboxylic acids with resorcinol, J von Braun et al Ber. 74B 1772–1783 (1941).

Fries transformations of condensates of sebacic acid with phenols: 1,8-dibenzoyloctanes, J P Varma et al, *J.Indian Chem.Soc.* 36 41–45 (1959).

The $Ca^{2+}$—stimulated, $Mg^{2+}$—dependent, adenosine triphosphatase ($Ca^{2+}$-ATPase) located on plasma membranes extrudes $Ca^{2+}$ against its electrochemical $Ca^{2+}$ gradient. It has been reported that $Ca^{2+}$-ATPase not only plays a fundamental role in regulating the total cellular $Ca^{2+}$ concentration but also modulates or mediates the effects of $Ca^{2+}$ mobilising hormones and neurotransmitters. (See Pripic V, Green K C, Blacknore P R and Exton J H Vasopressin-, angiotensin II-, and $α_1$-adrenergic-induced inhibition of $Ca^{2+}$-transportation by rat liver plasma membrane vesicles, (1984) *J.Biol.Chem.* 259, 1382–1385 and Rega A F, Garahan P J, (1986) The Ca Pump of Plasma membranes, CRC Pres Inc., Florida.

Natural and synthetic compounds of formula (I) were tested for their ability to influence human erythrocyte plasma membrane $Ca^{2+}$-ATPase. The enzyme $Ca^{2+}$-ATPase in the human red blood cell plasma membrane has previously been studied and its stimulation by calmodulin and activation by lipids and proteolysis and its primary structure have been published (see Carafoli E (1991) Calcium pump of the plasma membrane, *Physiological Reviews* 71, 129–153.

The activity of compounds of formula (I) in the inhibition of $Ca^{2+}$-ATPase is shown in Table 1 and is interpreted graphically in FIGS. 1, 2, 3 and 4.

Table 1: Structures and $IC_{50}$ values of natural and synthetic compounds of formula (I) in the inhibition of $Ca^{2+}$-ATPase (inhibition was determined at a concentration of 100 μM).

| COMPOUND | SOURCE | INHIBITION OF $Ca^{2+}$-ATPase PERCENT (%) | $IC_{50}$ (μM) |
|---|---|---|---|
| 2-octylphenol | b | 100 | 32 |
| 2-nonylphenol | b | 95 | 30 |
| 2-nonanoylphenol | b | 32 | >100 |
| 2-decylphenol | b | 85 | 42 |
| nonylphenol (commercial) | a | 100 | 27.5 |
| 4-octylphenol | b | 28 | 92 |
| 4-tert-octylphenol | a | 94 | 60 |
| 3-nonylphenol | b | 69 | 64 |
| 4-nonylphenol | b | 22 | 114 |
| 4-decylphenol | b | 24 | 170 |
| 2-cyclohexylphenol | h | 28 | 186 |
| 4-cyclohexylphenol | h | 16 | 271 |
| 1,10-bis(2-hydroxyphenyl)-decane | b | 100[i] | 7.6 |
| 1,12-bis(2-hydroxyphenyl)-dodecane | e | 100[i] | 8.3 |
| 1,14-bis(2-hydroxyphenyl)-tetradecane | e | 84 | 28 |
| 1-(2-hydroxyphenyl)-10-(4-hydroxyphenyl)decane | e | 100[j] | 12 |
| 1-(2-hydrozyphenyl)-12-(4-hydroxyphenyl)dodecane | e | 99 | 18.8 |
| 1-(2-hydroxyphenyl)-14-(4-hydroxyphenyl)-tetradecane | e | 60 | 81 |
| 1,10-bis(4-hydroxyphenyl)-decane | b | 52 | 93 |
| 1-(3,5-dihydroxy-phenyl)-14-(3,5-dihydroxy-4-methylphenyl)tetradecane (grebustol-A) | c | 100[j] | 17 |
| 1,14-bis(3,5-dihydroxy-4-methylphenyl)-tetradecane (striatol) | f | 98 | 16 |
| striatol-B | f | 100 | 40 |
| norstriatol-B | c | 61[k] | 35 |
| 5-nonylresorcinol | f | 44 | 108 |
| 1,14-bis(4-hydroxyphenyl)-tetradecane | b | 5 | 280 |
| 1,14-bis(3,5-dihydroxy-phenyl)tetradecane (bisnorstriatol) | f | 35 | >100 |
| 1,14-bis(3,5-dihydroxy-phenyl)tetradec-Z-6-ene (grebustol-B) | c | 90 | 50 |
| ethyl 2,4-dihydroxy-6-nonylbenzoate | f | 73 | 62 |
| ethyl 3,5-dibromo-2,4-dihydroxy-6-nonylbenzoate | f | 95 | 44 |
| grevillol | c | 44 | 143 |
| 5-decylresorcinol | f | 30 | 135 |
| ethyl 2,4-dihydroxy-6-decylbenzoate | f | 60 | 85 |
| ethyl 3,5-dibromo-2,4-dihydroxy-6-decylbenzoate | f | 73 | 69 |
| 2-E,E-farnesyl-5-methyl-resorcinol (grifolin) | d | 100 | 22.5 |
| 4-E,E-farnesyl-5-methyl-resorcinol (neogrifolin) | d | 100 | 23.3 |
| 4-dodecylresorcinol | a | 68 | 69 |
| 4-hexylresorcinol | a | 17 | 259 |

-continued

| COMPOUND | SOURCE | INHIBITION OF $Ca^{2+}$-ATPase | |
|---|---|---|---|
| | | PERCENT (%) | $IC_{50}$ ($\mu M$) |
| 2,4,6-tri-tert-butylphenol | a | 79 | 15 |
| 3,5-di-tert-butyl-catechol | a | 76 | 84 |
| 2,6-di-tert-butyl-4-methylphenol (BHT) | a | 69 | 66 |
| 2,6-di-tert-butylphenol | a | 61 | 79 |
| 2,6-di-tert-butyl-4-methoxyphenol (BHA) | a | 44 | >400 |
| 2,2'-methylenebis(4-methyl-6-tert-butylphenol) | g | 74 | 45 |

$^i$ — at 25 $\mu M$
$^j$ — at 50 $\mu M$
$^k$ — at 37 $\mu M$

The activity of the synthetic and natural compounds in the inhibition of $Ca^{2+}$-ATPase in the presence (+CaM) and in the absence (−CaM) of Calmodulin (CaM) is shown in table 1A below and is interpreted graphically in the FIGS. 5, 6, 7, 8, 9.

TABLE 1A

| SOURCE | COMPOUND | $IC_{50}$ | |
|---|---|---|---|
| | | (−CaM) | (+CaM) |
| b | 2-nonylphenol | 36 | 40 |
| b | 2-methyl-6-nonylphenol | — | — |
| b | 3-methyl-6-nonylphenol | 52 | 60 |
| b | 4-methyl-6-nonylphenol | 80 | 75 |
| b | 2-bromo-6-nonylphenol | — | — |
| b | 4-bromo-6-nonylphenol | 52 | 55 |
| b | 2,4-dibromo-6-nonylphenol | — | — |
| b | 2-nitro-6-nonylphenol | — | — |
| b | 4-nitro-6-nonylphenol | 80 | 70 |
| b | 2-bromo-4-nitro-6-nonylphenol | — | 70 |
| b | 4-bromo-2-nitro-6-nonylphenol | — | 65.5 |
| b | 4-nonylresorcinol | 125 | ND |
| a | 4-dodecylresorcinol | 80 | 100 |
| b | 2-bromo-6-nonylresorcinol | 400 | 400 |
| b | 4-bromo-6-nonylresorcinol | 400 | 400 |
| b | 2,4-dibromo-6-nonylresorcinol | — | — |
| b | 1,8-bis(2-hydroxyphenyl)octane | 24 | 24 |
| b | 1,9-bis(2-hydroxyphenyl)nonane | 13.5 | 14 |
| b | 1,10-bis(2-hydroxyphenyl)decane | 8.4 | 9.0 |
| e | 1,12-bis(2-hydroxyphenyl)dodecane | 12.5 | 13 |
| b | 1,10-bis(2-hydroxy-3-methylphenyl)-decane | 50 | 55 |
| b | 1,10-bis(2-hydroxy-4-methylphenyl)-decane | 29 | 29 |
| b | 1,10-bis(2-hydroxy-5-methylphenyl)-decane | 22 | 20.5 |
| b | 1,8-bis(2,4-dihydroxyphenyl)octane | 50 | 48 |
| b | 1,10-bis(2,4-dihydroxyphenyl)decane | 10 | 16 |
| e | 1,11-bis(2,4-dihydroxyphenyl)undecane | 25 | 21.7 |
| e | 1,12-bis(2,4-dihydroxyphenyl)dodecane | 12 | 20 |
| e | 1,10-bis(2,4-dihydroxy-3-methylphenyl)decane | 100 | 100 |
| b | 1,10-bis(3-hydroxyphenyl)decane | 30 | 32 |
| e | 1,10-bis(3-hydroxy-4-methylphenyl)-decane | 51 | 48 |
| b | 1,10-bis(4-hydroxy-3-methylphenyl)-decane | 100 | 94 |
| b | 1,1-bis(2-hydroxyphenyl)decane | 74 | 68 |
| e | 1,10-bis(2-hydroxy-1-naphthyl)decane | 92 | 90 |
| e | 6-dodecyl-7-hydroxy-4-methylcoumarin | NA | NA |
| b | 2-methyl-5-nonyl-resorcinol | NA | NA |
| i | 5,7,2',6'-tetrahydroxy-8-lavandulylflavanone | 20 | ND |
| i | 5,7,6'-trihydroxy-8-lavandulylflavanone | 26.5 | ND |
| i | 5,2',6'-trihydroxy-8-lavandulyl-7-methoxyflavanone | 45.3 | ND |

NA: no inhibitory activity;
ND: not determined
Source
a = commercially available from Aldrich, Milwaukee, WI, USA
b = synthetic preparation from literature procedure
c = extracted from Grevillea
d = natural products provided by Prof Shibata [Misasa H, Matsue Y, Vehara H, Tanaka H, Ishihara M, Shibata H, (1992) Tyrosinase inhibitors from *Albatrellus confluens*, Biosci.Biotech.Biochem., 56 1660–1661]
e = novel compounds of formula (II) according to the present invention
f = natural and synthetic substances provided by Prof W C Taylor [see references, page 9, lines 25–30 also Cleaver L, Croft J A, Ritchie E and Taylor W C (1976) Chemical studies of the Proteaceae IX Aust.J.Chem., 29, 1989–2001]
g = commercially available from Merck, Darmstardt, Germany
h = synthetic substance provided by Prof Kanzo Sakata, Shizuoka University, Shizuoka Japan [see reference for cyclohexylphenols (ortho & para) on page 17
i = natural substances provided by Assoc. Prof. C Chaichantipyuth, Chulalongkorn University of Thailand (see Ruangrungsi N et al, Photochemistry, 31, 999–1001, 1992 and Iinuma M et al, Photochemistry, 33, 203–208, 1993.

The potency of a compound for $Ca^{2+}$-ATPase inhibition is characterised by either its % inhibition at a single dose or more informatively as its $IC_{50}$ value from the dose-response curve. The most potent compounds have, therefore, curves located at the left hand side of the graphs. From FIG. 2, it can be seen that 1,10-bis(2-hydroxyphenyl)decane and, to a lesser extent, 1,12-bis(2-hydroxyphenyl) dodecane have the strongest $Ca^{2+}$-ATPase inhibition among the synthesised phenolic compounds. The inhibitory activity is two-fold higher than that of the natural product 1,14-bis(3,5-dihydroxy-4-methylphenyl)tetradecane (striatol) and is superior to the 2-alkylphenol series. Of the alkylphenols, the maximum activity appeared with 2-nonylphenol ($IC_{50}$=30 $\mu$m). The results of nonylphenols and octylphenols showed that the potency order of alkylphenols was 2-alkylphenols, 4-branched alkylphenols, and 4-alkylphenols. Similarly, 4-dodecylresorcinol was the most potent among the alkylresorcinols tested and grifolin and neogrifolin the most potent among the alkyl and alkenyl resorcinols tested.

The results also show the importance of substitution at the 2- position of the phenol ring for strong $Ca^{2+}$-ATPase inhibition. The results indicate that there is a significant difference in potency between ortho- and para- substituted compounds, whereas the activity of the meta- substituted compound is intermediate.

The results further indicate a structural preference for the inhibitory potency of the synthetic compounds and an optimal methylene chain length for the bis compounds is ten. 1,10-bis(2-hydroxyphenyl)decane and 1,10-bis(2,4-dihydroxyphenyl)decane to lesser extent are the most potent inhibitors of plasma $Ca^{2+}$-ATPase among the synthesised substances.

In the presence or absence of Calmodulin (CaM), in general, there is no significant difference in the inhibitory activity of the synthesised compounds (refer to table 1A). However, it is observed that at higher concentration of the test compounds, there was slightly higher inhibition of plasma membrane $Ca^{2+}$-ATPase than in the absence of CaM (refer to FIGS. 5,7,8,9). This would indicate that the compounds may also inhibit CaM stimulant activity.

$^{45}Ca$ efflux from cultured vascular smooth muscle cells consists of two major mechanisms; one is dependent on extracellular sodium, mediated by the $Na^+$-$Ca^{2+}$ exchanger ($Na^+$- dependent $Ca^{2+}$ efflux), and the other is independent of extracellular sodium but is mediated by the $Ca^{2+}$ pump ($Na^+$- independent $Ca^{2+}$ efflux). The effect of striatol on the efflux of calcium ($^{45}Ca^{2+}$) from rat thoracic aorta smooth muscle cells in culture was studied. $^{45}Ca^{2+}$ efflux is a measure of plasma membrane $Ca^{2+}$-ATPase (plus $Na^+$: $Ca^{2+}$ exchange) in intact (whole) cells. The results are as follows:

20 μM 5 min—partial inhibition
20 μM 10 min—partial inhibition
50 μM 30 min—complete inhibition Compounds of formula (I) show significant inhibitory activity against plasma membrane $Ca^{2+}$-ATPase and typically would be suitable for use in the treatment of cardiovascular disease. These compounds would be useful by their action on $Ca^{2+}$-ATPase enzymes in general or on $Na^+$, $K^+$-ATPase enzyme. In particular, compounds of formula (I) may be suitable for the treatment or prophylaxis of chronic heart failure, angina, hypertension or arrhythmia.

Accordingly, in another aspect, the present invention provides the use of a compound of formula (I) or a pharmaceutically acceptable derivative thereof in the manufacture of a medicament for the treatment or prophylaxis of cardiovascular disease.

The effective amount of the active compound required for use in the above conditions will vary both with the route of administration, the condition under treatment and the host undergoing treatment, and is ultimately at the discretion of the physician. In the above mentioned treatments, it is preferable to present the active compound as a pharmaceutical formulation. A pharmaceutical formulation of the present invention comprises the active compound together with one or more pharmaceutically acceptable carriers and optionally any other therapeutic ingredient. The formulation may conveniently be prepared in unit dosage form and may be prepared according to conventional pharmaceutical techniques. Additionally, the formulations may include one or more accessory ingredients, such as diluents, buffers, flavouring agents, binders, disintegrants, surface active agents, thickeners, lubricants, preservatives and the like.

A typical tablet formulation comprises 1–50 mg of the active constituent, 50–200 mg of lactose, 7–28 mg of maize starch and 0.25–1 mg of magnesium stearate. Preferably, the tablet formulation comprises 1–50 mg of the active constituent, about 97 mg of lactose, about 14 mg of maize starch and about 0.5 mg of magnesium stearate.

Compounds of formula (I) may also be useful for the treatment of ulcers (peptic ulcers) through $H^+$, $K^+$-ATPase inhibition (the proton pump in gastric parietal cells) or may act as depigmentation, antidiabetic, antithrombolytic, antiarteriosclerotic, antioxidant, anticancer, antiinflammatory or antiviral agents.

EXPERIMENTAL—SYNTHESES
Instrumentation

Thin layer chromatographic plates were visualised by a UVSL-58 mineral-light lamp, multiband UV-254/366 nm. Precoated Si gel plates (Merck, Art. 5554) were utilised.

Analytical high-performance liquid chromatography were obtained with a Beckman 110B solvent module with a PC-3800 controller.

Detection was achieved with a Spectra-Physics Spectra 100 variable wavelength detector.

Analytical column was an Activon exsil 100/10 ODS, 250×4.6 mm i.d. (reversed-phase $C_{18}$).

Preparative short column was 70×65 mm i.d. connected with an one litre glass bell jar.

$^1H$- and $^{13}C$-NMR spectra were obtained on a Varian Gemini 300 , and Joel FX90Q (for grevillol) spectrometer using $CDCl_3$ as solvent and referencing to tetramethylsilane.

UV spectra were measured on a Perkin-Elmer Lambda 5 UV/VIS spectrophotometer.

Chemical ionisation and electron impact mass spectra were performed on a Finnigan TSQ46 spectrometer. All chemical ionisation spectra were performed using methane as reagent gas.

Materials

Ethyl acetate and petroleum (70°–75° C.) were distilled prior to use. Thionyl chloride was distilled at 75°–80° C.

Dichloromethane, chloroform, methanol were HPLC grade. Merck silica gel 60H (Art. 7736) was used for preparative TLC and short column chromatography.

3,4,5-trimethoxybenzaldehyde, n-butyllithium, undecandioic acid, 1,6-dibromohexane, 1,8-dibromooctane, 1,10-dibromodecane, 1,12-dibromododecane, 2-methylresorcinol, 1,10-decanedicarboxylic acid and 1,12-dodecanedicarboxylic acid were purchased from Aldrich Chemical company.

I. Synthesis of alkylphenols

1.Preparation of 2- and 4-octylphenol 1.1 Preparation of phenyl octanoate

The ester was prepared by slowly adding thionyl chloride (10 ml) to a mixture of pure phenol(6.5 g) and octanoic acid(10 g). The reaction mixture was warmed to drive off the sulfur dioxide and hydrogen chloride gases. The crude mixture was distilled at 95°–100° C./5 mmHg.

Phenyl nonanoate and phenyl decanoate were prepared similarly. The esters were distilled at 105°–110° C. and 120°–125° C./5 mmHg respectively.

The yield of the esters was 81–84%.

1.2.Preparation of 2- and 4-octanoylphenol

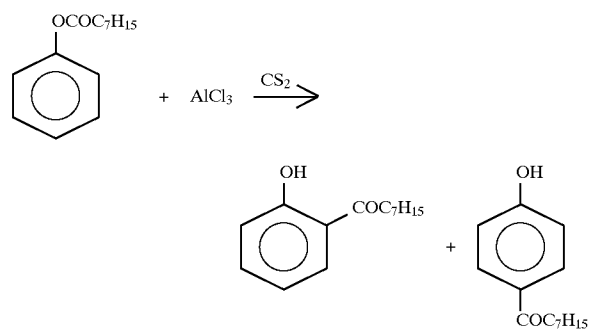

Anhydrous aluminium chloride(7 g) and carbon disulfide(10 ml) were placed in a three-necked round bottom flask fitted with a reflux condenser, a 50 ml-dropping funnel and a large magnetic stirrer. Phenyl octanoate(10 g) was slowly added to the stirred suspension through the dropping funnel. When all the ester was added, the mixture was further heated to gentle refluxing on a steam bath until the evolution of hydrogen chloride had almost ceased (about ½ hr). The reflux condenser was turned downward and carbon disulfide was distilled. The steam bath was replaced by an oil bath which was heated to 140° C. and maintained at 140°–150° C. for one hour. The mixture thickened and finally congealed to a brown resinous mass. The solid was allowed to cool and the aluminium complex was decomposed by first slowly adding a mixture of concentrated hydrochloric acid(6 ml) with water(6 ml) and then water(10 ml). The mixture was left overnight and large solid portion (mainly 4-octanoylphenol) on the surface was collected. The liquid portion was extracted with ethyl acetate. The extract was combined with the solid portion and the resulting mixture was dried with anhydrous sodium sulfate, filtered and evaporated to obtain the crude mixture. The products, 2- and 4-octanoylphenols, were separated by short column vacuum chromatography based on the difference in their polarity.

The yield was 29–34% of 2-octanoylphenol and 46–50% of 4-octanoylphenol. The products were then characterised by NMR and CI-MS analysis (refer to tables 3 & 4).

Separation of the products using short column vacuum chromatography

The crude mixture was dissolved firstly in dichloromethane (one-part) then petroleum (four-parts). The resulting mixture (25 ml) was loaded onto a (70 mm diam.×30 mm) silica gel bed under vacuum and continuously washed with petroleum (40 ml).

Eluent solvent mixtures used to isolate the products were a stepwise solvent gradient from petroleum spirit/ethyl acetate 9:1 to 1:1 (20 fractions).

Fractions were examined under UV light by TLC to determine the degree of separation between products. NMR and CI-MS analysis were performed on fractions #5–10 (identified as 2-octanoylphenol) and #14–20 (identified as 4-octanoylphenol).

1.3.Preparation of 2- and 4-octylphenol

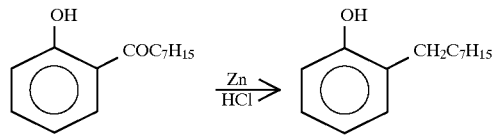

Amalgamated zinc(10 g) was placed in a 100 ml round-bottom flask fitted with a stirrer and a reflux condenser. A mixture of acetic acid(10 ml) and concentrated hydrochloric acid(10 ml) was added and then a solution of 2-octanoylphenol (2 g) (or 4-octanoylphenol) in acetic acid(5 ml). The mixture was agitated and refluxed for 2 days. Aqueous 20% w/v NaCl solution(20 ml) was added and the mixture was extracted with petroleum(20 ml). The petroleum portion was dried with anhydrous sodium sulfate, filtered and purified by short column vacuum chromatography.

A yield of 82–84% was obtained.

The column chromatographic method used was the same as described above.

The products were characterised by NMR and CI-MS analysis (Refer to tables 3 & 4). Note: 1. The zinc was amalgamated in the reaction flask by covering it with a solution of mercuric chloride(0.2 g) in water(15 ml) and occasionally agitated over 30 minutes. The solution was poured off and the zinc was rinsed once with water.

2. Aqueous 20% w/v NaCl was added to increase the ionic strength of the aqueous phase so that the octylphenol could be extracted into the organic phase.

Nonyl- and decylphenols were prepared as described for octylphenol. The products at each stage were also characterised by NMR and CI-MS analysis. (Refer to tables 3 & 4).

2. Preparation of 3-nonylphenol 2.1 Preparation of 3-benzyloxybenzaldehyde

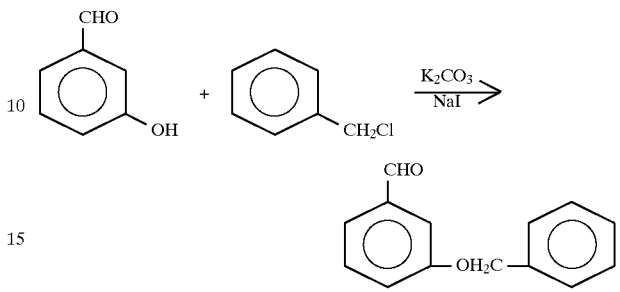

In a 100 ml round-bottom flask were placed 3-hydroxybenzaldehyde (5 g), benzyl chloride(6 g), sodium iodide(8 g) and potassium carbonate(10 g). The reaction mixture was sealed and stirred for one day. The crude product was extracted with ethyl acetate (20 ml). The organic portion was washed twice with distilled water(20 ml) to remove all aqueous soluble materials. The ethyl acetate portion was dried with anhydrous sodium sulfate and evaporated to obtain the crude solid. The solid was purified by the column chromatographic method described for octylphenol. The product was identified by NMR and CI-MS analysis (Refer to tables 3 & 4).

2.2 Preparation of 3-nonylphenol

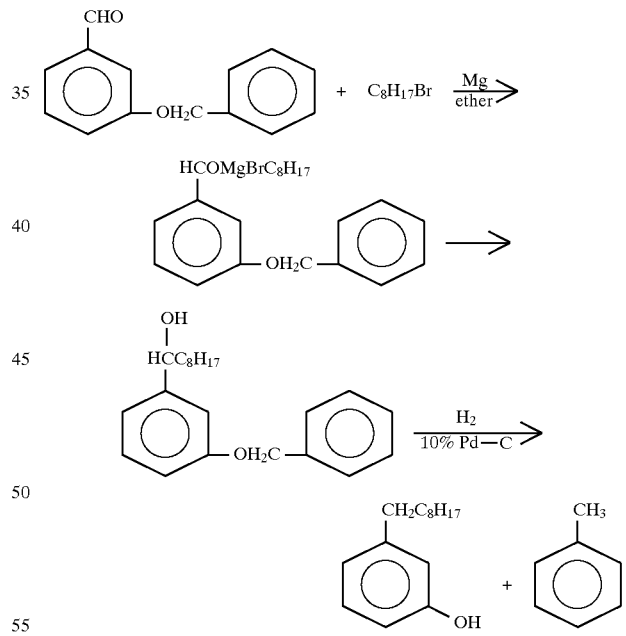

Grignard reagent was prepared from magnesium(248 mg) and 1-bromooctane(1.8 g) in dry diethyl ether(5 ml). A tiny amount of solid iodine was added to initiate the reaction and ether(10 ml) was further added. The reaction was stirred until all magnesium dissolved and 3-benzyloxybenzaldehyde(10 g) was then added to the reaction mixture. The reaction was refluxed at room temperature for 4 hours. Ice water was then added. The organic phase was separated and washed with 1.5M sulfuric acid (2×25 ml), 10% potassium carbonate (2×25 ml), water (20 ml), 1M hydrochloric acid (20 ml) in saturated sodium chloride, dried with anhydrous sodium sulfate and evaporated to obtain the product (79% of yield).

A portion of the product—(500 mg) was hydrogenated by catalytic reduction over 10% palladium-charcoal(130 mg) in ethyl acetate (50 ml) containing concentrated sulfuric acid (10 drops). The reaction mixture was stirred at room temperature for one day. The mixture was then filtered, evaporated and purified by the column chromatographic method.

The product was identified by NMR and CI-MS analysis (Refer to tables 3 & 4).

II. Synthesis of α,ω-bis(hydroxyphenyl)alkanes.
1. Preparation of bisphenyl decanedioate

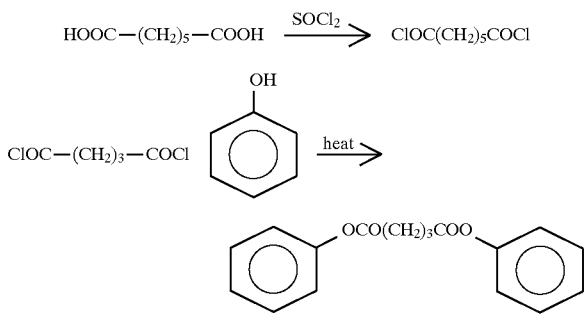

The methods of preparation, isolation and purification were similar to those described for octylphenol except that the preparation of esters was done in two separate steps, as shown above, instead of one as described for phenyl octanoate.

Firstly, the acid dichloride was prepared by refluxing the mixture of dicarboxylic acid(5 g) and thionyl chloride(20 ml) at 60°–70° C. for two hours. Thionyl chloride was then removed by evaporation and the remaining product was dissolved in toluene(5 ml). The toluene was evaporated to remove all traces of thionyl chloride.

Secondly, the phenol(2× moles of acid dichloride) was added to the acid dichloride. The mixture was warmed to drive off hydrogen chloride gas. The product solidified on cooling and was purified by the column chromatographic method.

The yield of the esters was 96–98%

2. Preparation of 1,10-bis(hydroxyphenyl)decane-1,10-diones

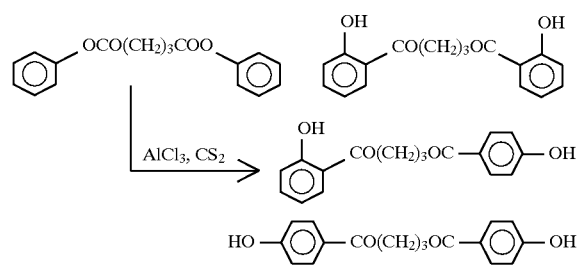

3. Preparation of 1,10-bis(2-hydroxyphenyl)decane

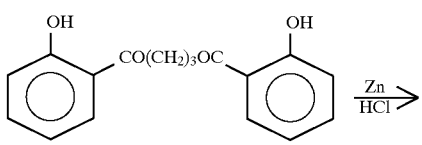

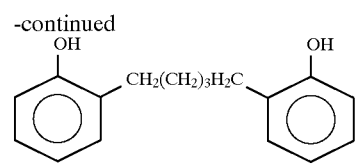

The product was characterised by NMR and CI-MS analysis (Refer to NMR and CI-MS tables 3 & 4).

III. Synthesis of α,ω-bis[2-hydroxy-(3-,4- or 5-methyl)phenyl]alkanes

These were prepared according to K Kakemi et al. in Antioxidants III. K Kakemi, Y Arita, R Hori and H Takenaka. Yakugaku Zashi 86, 791–796 (1966) as follows: Aliphatic dicarboxylic acid chloride (1 mole) [for example sebacoyl chloride] was added to a solution of a phenol (2.2 moles) in tetrachloroethane containing anhydrous $AlCl_3$ (2.5 moles). The mixture was stirred for 5–6 hrs at 70°–80° C. The product was decomposed with ice-water and concentrated HCl (1:1). The organic layer was separated and concentrated under reduced pressure. The residue was extracted with ethyl acetate and washed with water twice. After removal of the solvent the product was subjected to gradient chromatography to isolate the corresponding diketones which on Clemmensen reduction gave the title compounds.

The products were recrystallised from petroleum or petroleum—ethyl acetate to give colourless crystalline solids.

The procedure was similarly applied to prepare bis(2-hydroxy-1-naphthyl)decane.

IV. 1,10-Bis(4-hydroxy-3-methylphenyl)decane

This was prepared by the method reported by Schlack and Koller in Aromatic aliphatic diketones. P Schlack and W Koller. Ger. 1,086,711 Aug. 11, 1960. The title compound was prepare by treatment of orthocresol (2.2 moles) with sebacic acid (1 mole) in the presence of polyphosphoric acid (3 moles). The mixture was stirred for 4 hrs at 80° C. and poured to ice-water after cooling. The precipitant was filtered, dissolved in ethyl acetate and washed with water three times. The solvent was evaporated to yield a crude 1,10-bis(4-hydroxy-3-methylphenyl)decane-1,10-dione which was then subjected to Clemmensen reduction to give the title compound.

The product was recrystallised to yield a colourless crystalline white solid.

V. Synthesis of α,ω-bis(2.4-dihydroxy-(3-methyl)phenyl)alkanes

These were prepared according the literature procedure in Reactions of aliphatic dicarboxylic acids with resorcinol. J von Braun, E Anton and F Meyer. Ber. 74B, 1772–1783 (1941) as follows: The aliphatic dicarboxylic acid (1 mole) was heated with anhydrous $ZnCl_2$ (2 moles) at 140° C. followed by added resorcinols (10 moles) in portions. Stirring of the mixture was maintained for 4–5 hrs at 140°–160° C. (except that for 2-methylresorcinol which was stirred at 170° C.). The products were decomposed with ice-water. The solid was collected, washed with 10% $Na_2CO_3$ and then with water under vacuum.

The crude products were subjected to Clemmensen reduction to yield the title compounds and were recrystallised from ethanol-water to give colourless crystalline solids.

VI. Synthesis of 1,10-bis[3-hydroxy-4-methylphenyl]decane.

1,10-Bis(4-methylphenyl)decane-1,10-dione was prepared according to (III) above. The diketone dissolved in concentrated sulfuric acid were gradually added to the mixture of fuming nitric acid and concentrated sulfuric acid (2:1 in volume) at −5° C. The mixture was stirred at 0° C. for 30 mins and poured in to ice-water. The precipitate was filtered off and recrystallised from ethyl acetate to give 1,10-bis(3-nitro-4-methylphenyl)decane-1,10-diones which then underwent reduction with $SnCl_2.2H_2O$ in the presence of concentrated HCl at elevated temperature of 90° C. for 30 mins. The precipitate that formed on cooling was collected, washed with HCl and dissolved in dilute NaOH. The solid precipitating on the addition of dilute HCl was collected and recrystallised from ethanol to yield 1,10-bis(3-amino-4-methylphenyl)decane-1,10-dione.

This product was diazotised with aq. $NaNO_2$ in 3M $H_2SO_4$ at 5° C. The mixture was then hydrolysed with 10% $H_2SO_4$ at 160° C. The resulting solution was extracted with ethyl acetate and the solvent was evaporated to yield 1,10—(bis(3-hydroxy-4-methylphenyl)decane-1,10-dione which on Clemmensen reduction and gave the title compound which was recrystallised from petroleum-dichloromethane.

VII. Synthesis of α,ω-bis(3.5-dihydroxy-4-methylphenyl)alkanes.

a. 3,5-dimethoxy-4-methylbenzaldehyde was prepared by a procedure published in Regioselective reduction alkylation of 3,4,5-trimethoxy-benzaldehydes and dimethylacetal. U Azzena, S Cossu, T Denurra, G Melloni and A M Piroddi. Synthesis 1990, 313 and Regioselective reduction electrophilic substitution of derivatives of 3,4,5-trimethoxybenzaldehyde. U Azzena, G Melloni, A M Piroddi, E Azara, S Contini and E Fenude. J. Org. Chem. 57, 3101–3106 (1992).

The diacetal intermediate was distilled at 130° C./0.8 mmHg and 3,5-dimethoxy-4-methylbenzaldehyde (compound A) was recrystallised from petroleum.

b. Preparation of α-N,N-dimethylamino-α-cyano-(3,5-dimethoxy-4-methyl)benzylidene (Compound B) (see Benzylation and related alkylation of α-dimethylaminophenylacetonitrile by mean of alkali. C R Hauser, H M Taylor and T G Ledford. J. Am. Chem. Soc. 82, 1786 (1960).

To a stirred solution of sodium bisulfite (1 mole) in 400 ml of water was added compound A (1 mole) in methanol followed by anhydrous dimethylamine (1.2 moles) in aq. methanol (80%). The reaction mixture was cooled prior the addition of aq. sodium cyanide (1.2 moles). The mixture was stirred at room temperature for 20 hrs and diethyl ether (50 ml) was then added. The ethereal layer was washed with water twice and evaporated to yield the product Compound B (>90%) which was sufficiently pure for the next reaction.

c. Preparation of α,ω-bis(3,5-dimethoxy-4-methylphenyl)alkane-α,ω-diones (see An efficient method for synthesis of symmetrical diketones via reaction of α-amino-α-arylacetonitriles with alkyl dibromides. K Takahashi, M Watsuzaki, K Ogura and H Iida. J. Org. Chem. 48, 1909–1912 (1983).

Under dry nitrogen diisopropylamine (1,5 ml, 9 mmol) dissolved in a mixture of 5 ml each of dry THF and HMPA was treated with n-butyllithium (4 ml of 2.5M solution in hexane, 10 mmol) at −78° C. Compound B (8 mmol) dissolved in THF (2 ml) was added and the reaction mixture was stirred for 15 mins at −78° C. and for 1 hr at 0° C. To the mixture cooled to −20° C. was added α,ω-dibromoalkanes (4 nmol) dropwise. After the mixture was stirred for 20 mins at −20° C., the stirring was continue overnight at room temperature.

The reaction mixture was poured into ice-water and extracted with diethyl ether (3×50 ml). The combined ethereal layers was washed with brine and concentrated under reduced pressure. The residue dissolved in a solution of 3 ml each of THF and 30% aq. oxalic acid was refluxed for 90 mins then extracted with diethyl ether. After the solvent was evaporated the product was recrystallised from ethanol to give the diketones (Compounds C).

d. Preparation of α,ω-bis(3,5-dihydroxy-4-methylphenyl) alkanes.

The Compounds C were subjected to Clemmensen reduction and then demethylation with 47% HBr in the presence of acetic acid at 130° C. for 10 hrs. The product was subjected to gradient chromatography and recrystallised from benzene to give a colourless crystalline solid.

1,1-Bis (2-hydroxyphenyl) decane was prepared according to the literature procedure of G Casiraghi et al. in Regiospecificity in reactions of metal phenoxides. Synthesis of 2,2-alkylidenebisphenols. G Casiraghi, G Casnati, A Pochini and R Ungaro. J. Chem. Soc.,Perkin Trans.1 (1982), 3, 805–808. The product was distilled at 210° C./0.4 mmHg.

6-dodecyl-7-hydroxy-4-methylcoumarin was prepared according to the literature procedure of S P Starkov et al. in Condensation of ethyl acetoacetate and ethyl benzoylacetate with 4-alkylresorcinols in the presence of boron trifluoride etherate. S P Starkov, G A Goncharenko and A I Panasenko. Zh. Obshch. Khim. (1993), 63(5), 1111–1115.

The product was recrystallised from ethanol.

Bromination of 2-nonylphenol was carried out according to D E Rearson et al. in The ortho bromination of phenols. D E Rearson, R D Wysong and C V Breder. J. Org. Chem. (1967), 35(19), 3221–3231.

Nitration of 2-nonylphenol was carried out according to D S Ross et al. in Catalysis of aromatic nitration by the lower oxides of nitrogen. D S Ross, G P Hum and W G Blucher. J. Chem. Soc., Chem. Comm. 1980, 532–533. Bromination of 4-dodecylresorcinol was carried out according to E Kiehlmann and R W Lauener in Bromophloroglucinols and their methyl ethers. E Kiehlmann and R W Lauener. Can. J. Chem. (1989), 67, 335–344.

4-bromo-6-dodecylresorcinol was prepared according to procedure 8 above in The ortho bromination of phenols. D E Rearson, R D Wysong and C V Breder. J. Org. Chem. (1967), 35(19), 3221–3231.

* Clemmensen reduction was carried out as follows:

The ketone compounds dissolved in toluene were added to the mixture of concentrated HCl and acetic acid (1:1) containing amalgamated zinc. The reaction mixture was refluxed for 10 hrs with vigorous stirring or stirred at room temperature for 2 days.

TABLE 2

Synthetic phenolic products

| COMPOUND (No) | MELTING POINT °C. | % YIELD |
|---|---|---|
| 2-octylphenol (1) | | 19.8–23.3 |
| 2-decylphenol (3) | | |

TABLE 2-continued

Synthetic phenolic products

| | MELTING POINT °C. | % YIELD |
|---|---|---|
| 4-octylphenol (4) m.p. 40–42° C. | | 31.5–34.2 |
| 4-nonylphenol (5) m.p. 27–38° C. | | 31.5–34.2 |
| 4-decylphenol (6) m.p. 53–55° C. | | |
| 3-nonylphenol (7) | | 10.0 |
| 1,14-bis(2-hydroxyphenyl)tetradecane (14) | | 20.8–23.3 |
| 1-(2-hydroxyphenyl)-10-(4-hydroxyphenyl)decane (9) | | 22.5–25 |
| 1-(2-hydroxyphenyl)-12-(4-hydroxyphenyl)dodecane (12) | | |
| 1-(2-hydroxyphenyl)-14-(4-hydroxyphenyl)tetradecane (15) | | |
| 1,10-bis(4-hydroxphenyl)decane (10) | | 6.7–8.3 |
| 1,12-bis(4-hydroxyphenyl)dodecane (13) | | |
| 1,14-bis(4-hydroxyphenyl)tetradecane (16) | | |
| COMPOUNDS | | |
| 2-nonylphenol (2) | liq. | 58–60 |
| 2-methyl-6-nonylphenol | liq. | 56 |
| 3-methyl-6-nonylphenol | liq. | 52 |
| 4-methyl-6-nonylphenol | liq. | 50 |
| 2-bromo-6-nonylphenol | liq. | 40 |
| 4-bromo-6-nonylphenol | 45–47 | 85 |
| 2,4-dibromo-6-nonylphenol | liq. | >95 |
| 2-nitro-6-nonylphenol | liq. | 45 |
| 4-nitro-6-nonylphenol | liq. | 38 |
| 2-bromo-4-nitro-6-nonylphenol | 64–65 | >90[a] |
| 4-bromo-2-nitro-6-nonylphenol | 61–63 | |
| 4-nonylresorcinol | 70–71 | 80 |
| 2-bromo-6-dodecylresorcinol | 68–69 | 70[b] |
| 4-bromo-6-dodecylresorcinol | 61–62 | 82 |
| 2,4-dibromo-6-dodecylresorcinol | 58–59 | >95 |
| 6-dodecyl-7-hydroxy-4-methyl-coumarin | 135–136 | 75 |
| 1,8-bis(2-hydroxyphenyl)octane | 74 | 40–45 |
| 1,9-bis(2-hydroxyphenyl)nonane | 64–65 | |
| 1,10-bis(2-hydroxyphenyl)decane (8) | 81–82 | |
| 1,12-bis(2-hydroxyphenyl)dodecane (11) | 88.5 | |
| 1,10-bis(2-hydroxy-3-methylphenyl)decane | 82–83 | 38 |
| 1,10-bis(2-hydroxy-4-methylphenyl)decane | 102–103 | 40 |
| 1,10-bis(2-hydroxy-5-methylphenyl)decane | 86 | 25 |
| 1,8-bis(2,4-dihydroxyphenyl)octane | 167–168 | 75–80 |
| 1,10-bis(2,4-dihydroxyphenyl)decane | 155–156 | |
| 1,11-bis(2,4-dihydroxyphenyl)undecane | 136–137 | |
| 1,12-bis(2,4-dihydroxyphenyl)dodecane | 146–147 | |
| 1,10-bis(2,4-dihydroxy-3-methylphenyl)decane | 138–140 | 70 |
| 1,10-bis(3-hydroxyphenyl)decane | 71–73 | 18–20 |
| 1,10-bis(3-hydroxy-4-methylphenyl)decane | 100–102 | |
| 1,10-bis(4-hydroxy-3-methylphenyl)decane | 82–83 | 78 |
| 1,1-bis(2-hydroxyphenyl)decane | liq. | 70 |
| 1,10-bis(2-hydroxy-1-naphthyl)decane | 101–103 | 40 |
| 2-methyl-5-nonyl-resorcinol | 91–92 | 70 |
| 1,8-bis(3,5-dihydroxy-4-methylphenyl)octane | 173–175 | 65–70 |
| 1,10-bis(3,5-dihydroxy-4-methylphenyl)decane | 139–140 | |
| 1,12-bis(3,5-dihydroxy-4-methylphenyl)dodecane | 123–124 | |
| 1,14-bis(3,5-dihydroxy-4-methylphenyl)tetradecane | 130–131 | |

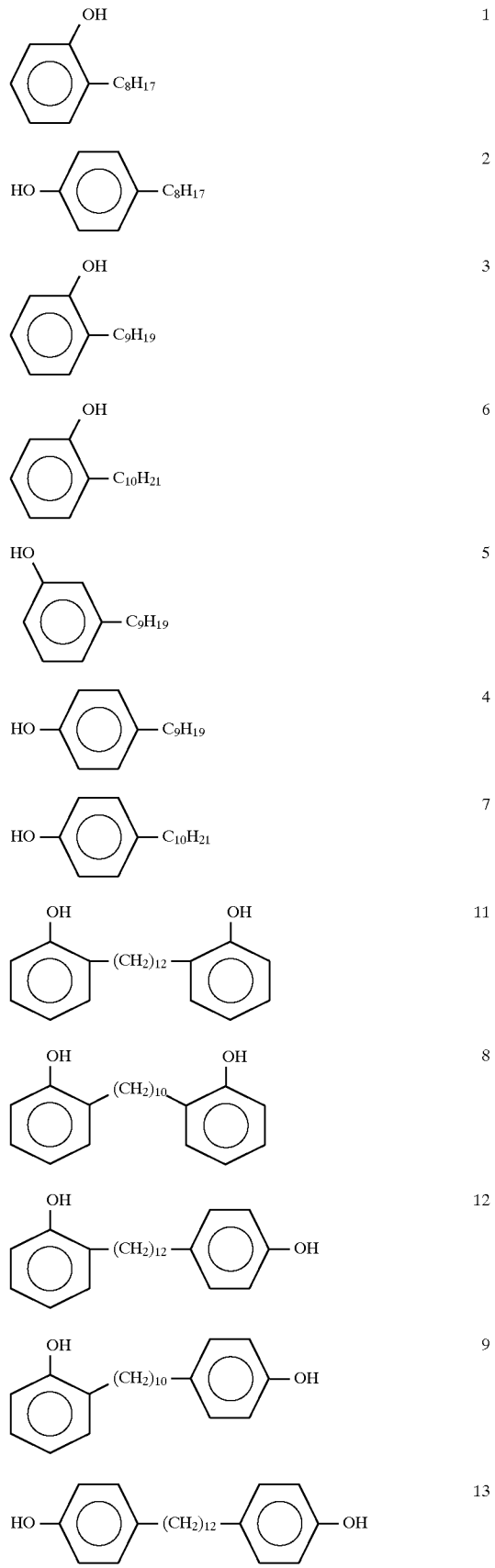

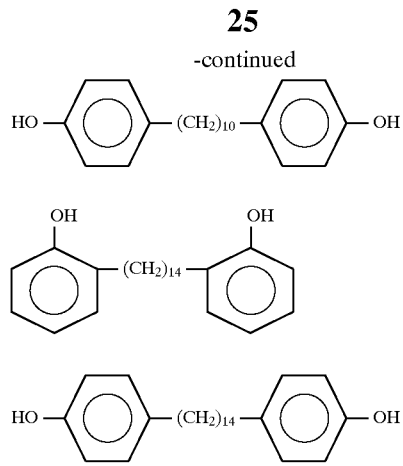

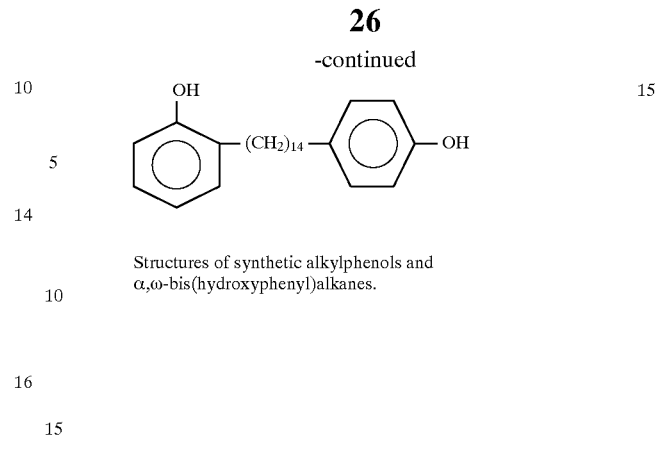

Structures of synthetic alkylphenols and α,ω-bis(hydroxyphenyl)alkanes.

TABLE 3

$^1$H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|
| $^1$H-NMR spectra of the intermediate products | | | | |
| 2-alkanoylphenols | 0.88 | 3 | t (b) | —CH$_3$ |
| 2-octanoylphenol (n = 4) | 1.3 | 8 | m (b) | —CH$_2$— |
| 2-nonanoylphenol (n = 5) | 1.3 | 10 | m (b) | —CH$_2$— |
| 2-decanoylphenol (n = 6) | 1.3 | 12 | m (b) | —CH$_2$— |
| | 1.7 | 2 | q (b) | Hf |
| | 2.9 | 2 | t | He |
| | 6.88 | 1 | dt | Hc |
| | 6.98 | 1 | dd | Ha |
| | 7.45 | 1 | dt | Hb |
| | 7.77 | 1 | dd | Hd |

$J_{ab}$ = 8 Hz, $J_{ac}$ = 2 Hz, $J_{bc}$ = 8 Hz, $J_{bd}$ = 2 Hz, $J_{cd}$ = 8 Hz

| Compound | δ in ppm | No of protons | Multiplicity | Assignment |
|---|---|---|---|---|
| 4-alkanoylphenols | 0.88 | 3 | t (b) | —CH$_3$ |
| 4-octanoylphenol (n = 4) | 1.30 | 8 | m (b) | —CH$_2$— |
| 4-nonanoylphenol (n = 5) | 1.30 | 10 | m (b) | —CH$_2$— |
| 4-decanoylphenol (n = 6) | 1.30 | 12 | m (b) | —CH$_2$— |
| | 1.70 | 2 | q (b) | Hd |
| | 2.90 | 2 | t | Hc |
| | 6.89 | 2 | d | Hb |
| | 7.80 | 2 | d | Ha |

$J_{ab}$ = 8 Hz

TABLE 3-continued

¹H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|

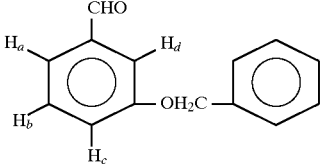

| 3-benzyloxybenzaldehyde | 5.11 | 2 | s | $-CH_2-$ |
| | 7.24 | 1 | m | Hc |
| | 7.3–7.5 | 8 | m | Ar-H |
| | 9.96 | 1 | s | $-CHO$ |

$J_{bc} = 8$ Hz, $J_{ac} = 2$ Hz, $J_{cd} = 2$ Hz diphenyl alkanedioates

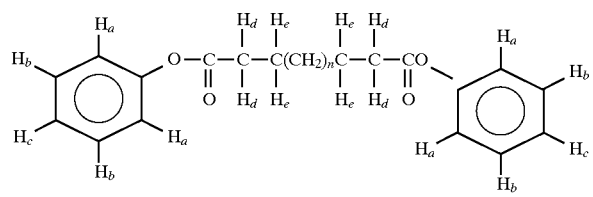

| diphenyl decanedioate (n = 4) | 1.33 | 8 | m (b) | $-CH_2-$ |
| bisphenyl dodecanedioate (n = 6) | 1.33 | 12 | m (b) | $-CH_2-$ |
| bisphenyl tetradecanedioate (n = 8) | 1.33 | 16 | m (b) | $-CH_2-$ |
| | 1.75 | 4 | q (b) | He |
| | 2.55 | 4 | t | Hd |
| | 7.08 | 4 | dd | Ha |
| | 7.20 | 2 | tt | Hc |
| | 7.36 | 4 | t | Hb |

$J_{ab} = 8$ Hz, $J_{ac} = 2$ Hz, $J_{bc} = 8$ Hz alpha, omega-bis(2-hydroxyphenyl)alkanediones

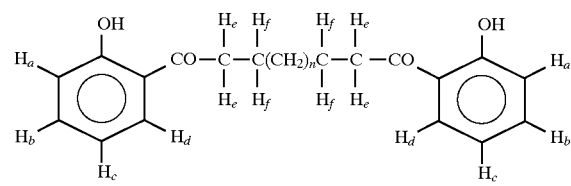

| 1,10-bis(2-hydroxyphenyl)decane-1,10-dione (n = 4) | 1.30 | 8 | m (b) | $-CH_2-$ |
| 1,12-bis(2-hydroxyphenyl)dodecane-1,12-dione (n = 6) | 1.30 | 12 | m (b) | $-CH_2-$ |
| 1,14-bis(2-hydroxyphenyl)tetradecane-1,14-dione (n = 8) | 1.30 | 16 | m (b) | $-CH_2-$ |
| | 1.75 | 4 | q (b) | Hf |
| | 2.98 | 4 | t | He |
| | 6.9 | 2 | dt | Hc |
| | 6.98 | 2 | dd | Ha |
| | 7.46 | 2 | dt | Hb |
| | 7.76 | 2 | dd | Hd |

$J_{ab} = 8$ Hz, $J_{ac} = 2$ Hz, $J_{bc} = 8$ Hz, $J_{bd} = 2$ Hz, $J_{cd} = 8$ Hz alpha-(2-hydroxyphenyl)-omega-(4-hydroxyphenyl)alkanediones TABLE 3-continued $^1$H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|

[Structure: alpha-(2-hydroxyphenyl)-omega-(4-hydroxyphenyl)alkanedione with labeled protons Ha, Hb, Hc, Hd on 2-OH-phenyl ring; Hi, Hm on CH carbons; Hm, Hg on other side; He, Hf on 4-OH-phenyl ring]

| Compound | δ in ppm | No of protons | Multiplicity | Assignment |
|---|---|---|---|---|
| 1-(2-OH-phenyl)-10-(4-OH-phenyl)decane-1,10-dione (n = 4) | 1.30 | 8 | m (b) | $-CH_2-$ |
| 1-(2-OH-phenyl)-12-(4-OH-phenyl)dodecane-1,12-dione (n = 6) | 1.30 | 12 | m (b) | $-CH_2-$ |
| 1-(2-OH-phenyl)-14-(4-OH-phenyl)tetradecane-1,14-dione (n = 8) | 1.30 | 16 | m (b) | $-CH_2-$ |
| | 1.72 | 4 | q (b) | Hm |
| | 2.92 | 2 | t | Hg |
| | 2.97 | 2 | t | Hi |
| | 6.89 | 1 | dt | Hc |
| | 6.92 | 2 | d | He |
| | 6.96 | 1 | dd | Ha |
| | 7.45 | 1 | dt | Hb |
| | 7.76 | 1 | dd | Hd |
| | 7.90 | 2 | d | Hf |

$J_{ab} = 8$ Hz, $J_{ac} = 2$ Hz, $J_{bc} = 8$ Hz, $J_{bd} = 2$ Hz, $J_{cd} = 8$ Hz, $J_{ef} = 8$Hz alpha, omega-bis(4-hydroxyphenyl)alkanediones

[Structure: symmetric bis(4-hydroxyphenyl)alkanedione with labeled protons Ha, Hb on rings; Hc, Hd on CH carbons]

| Compound | δ in ppm | No of protons | Multiplicity | Assignment |
|---|---|---|---|---|
| 1,10-bis(4-hydroxyphenyl)decane-1,10-dione (n = 4) | 1.3 | 8 | m (b) | $-CH_2-$ |
| 1,12-bis(4-hydroxyphenyl)dodecane-1,12-dione (n = 6) | 1.3 | 12 | m (b) | $-CH_2-$ |
| 1,14-bis(4-hydroxyphenyl)tetradecane-1,14-dione (n = 8) | 1.3 | 16 | m (b) | $-CH_2-$ |
| | 6.92 | 4 | d | Hb |
| | 7.9 | 4 | d | Ha |

$J_{ab} = 8$ Hz $^1$H-NMR spectra of the alkylphenols and alpha, omega-bis(hydroxyphenyl)alkanes

[Structure: 2-alkylphenol with labeled protons Ha, Hb, Hc, Hd on ring; He, Hf on CH carbons; $(CH_2)_nCH_3$]

| Compound | δ in ppm | No of protons | Multiplicity | Assignment |
|---|---|---|---|---|
| 2-alkylphenols | 0.88 | 3 | t (b) | $-CH_3$ |
| 2-octylphenol (n = 5) | 1.30 | 10 | m (b) | $-CH_2-$ |
| 2-nonylphenol (n = 6) | 1.30 | 12 | m (b) | $-CH_2-$ |
| 2-decylphenol (n = 7) | 1.30 | 14 | m (b) | $-CH_2-$ |
| | 1.60 | 2 | q (b) | Hf |
| | 2.60 | 2 | t | He |
| | 6.74 | 1 | dd | Ha |
| | 6.86 | 1 | dt | Hc |

TABLE 3-continued

¹H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|
| | 7.05 | 1 | dd | Hd |
| | 7.09 | 1 | dt | Hb |

$J_{ab} = 8$ Hz, $J_{ac} = 2$ Hz, $J_{bc} = 8$ Hz, $J_{bd} = 2$ Hz, $J_{cd} = 8$ Hz

[Structure: 4-alkylphenol with HO-C₆H₃(Hb,Ha)₂-C(Hc)₂-C(Hd)₂-(CH₂)ₙCH₃]

| Compound | δ in ppm | No of protons | Multiplicity | Assignment |
|---|---|---|---|---|
| 4-alkylphenols | 0.88 | 3 | t (b) | —CH₃ |
| 4-octylphenol (n = 5) | 1.28 | 10 | m (b) | —CH₂— |
| 4-nonylphenol (n = 6) | 1.28 | 12 | m (b) | —CH₂— |
| 4-decylphenol (n = 7) | 1.28 | 14 | m (b) | —CH₂— |
| | 1.56 | 2 | q (b) | Hd |
| | 2.52 | 2 | t | Hc |
| | 6.74 | 2 | d | Hb |
| | 7.02 | 2 | d | Ha |

$J_{ab} = 8$ Hz

[Structure: 3-nonylphenol with OH on ring, Ha, Hb, Hc, Hd positions, —C(He,Hf)—C(He,Hf)(CH₂)₆CH₃]

| Compound | δ in ppm | No of protons | Multiplicity | Assignment |
|---|---|---|---|---|
| 3-nonylphenol | 0.88 | 3 | t | —CH₃ |
| | 1.27 | 12 | m (b) | —CH₂— |
| | 1.58 | 2 | q (b) | Hg |
| | 2.54 | 2 | t | He |
| | 6.64 | 1 | dd | Ha |
| | 6.65 | 1 | d | Hd |
| | 6.74 | 1 | dd | Hc |
| | 7.13 | 1 | dt | Hb |

$J_{ab} = 8$ Hz, $J_{ac} = 2$ Hz, $J_{ad} = 2$ Hz, $J_{bc} = 8$ Hz, $J_{cd} = 2$ Hz alpha, omega-bis(2-hydroxyphenyl)alkanes

[Structure: HO-C₆H₃(Ha,Hb,Hc,Hd)-C(He,Hf)-C(He,Hf)-(CH₂)ₙ-C(Hf,He)-C(Hf,He)-C₆H₃(Hd,Hc,Hb,Ha)-OH]

| Compound | δ in ppm | No of protons | Multiplicity | Assignment |
|---|---|---|---|---|
| 1,10-bis(2-hydroxy phenyl)decane (n = 6) | 1.28 | 12 | m (b) | —CH₂— |
| 1,12-bis(2-hydroxy phenyl)dodecane (n = 8) | 1.28 | 16 | m (b) | —CH₂— |
| 1,14-bis(2-hydroxy phenyl)tetradecane (n = 10) | 1.28 | 20 | m (b) | —CH₂— |
| | 1.60 | 4 | q (b) | Hf |
| | 2.60 | 4 | t | He |
| | 6.75 | 2 | dd | Ha |
| | 6.86 | 2 | dt | Hc |
| | 7.06 | 2 | dd | Hd |
| | 7.10 | 2 | dt | Hb |

$J_{ab} = 8$ Hz, $J_{ac} = 2$ Hz, $J_{bc} = 8$ Hz, $J_{bd} = 2$ Hz, $J_{cd} = 8$ Hz alpha-(2-hydroxyphenyl)-omega-(4-hydroxyphenyl)alkanes

TABLE 3-continued $^1$H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|
| 1-(2-OH-ph)-10-(4-OH-ph)decane (n = 6) | 1.28 | 12 | m (b) | —CH$_2$— |
| 1-(2-OH-ph)-12-(4-OH-ph)dodecane (n = 8) | 1.28 | 16 | m (b) | —CH$_2$— |
| 1-(2-OH-ph)-14-(4-OH-ph)tetradecane (n = 10) | 1.28 | 20 | m (b) | —CH$_2$— |
|  | 1.60 | 4 | q (b) | Hm |
|  | 2.55 | 2 | t | Hg |
|  | 2.62 | 2 | t | Hi |
|  | 6.73 | 2 | d | He |
|  | 6.75 | 1 | dd | Ha |
|  | 6.86 | 1 | dt | Hc |
|  | 7.02 | 2 | d | Hf |
|  | 7.06 | 1 | dd | Hd |
|  | 7.10 | 1 | dt | Hb |

$J_{ab}$ = 8 Hz, $J_{ac}$ = 2 Hz, $J_{bc}$ = 8 Hz, $J_{bd}$ = 2 Hz, $J_{cd}$ = 8 Hz, $J_{ef}$ = 8 Hz
alpha, omega-bis(4-hydroxyphenyl)alkanes

| Compound | δ in ppm | No of protons | Multiplicity | Assignment |
|---|---|---|---|---|
| 1,10-bis(4-hydroxyphenyl)decane (n = 6) | 1.28 | 12 | m (b) | —CH$_2$— |
| 1,12-bis(4-hydroxyphenyl)dodecane (n = 8) | 1.28 | 16 | m (b) | —CH$_2$— |
| 1,14-bis(4-hydroxyphenyl)tetradecane (n = 10) | 1.28 | 20 | m (b) | —CH$_2$— |
|  | 1.60 | 4 | q (b) | Hd |
|  | 2.52 | 4 | t | Hc |
|  | 6.74 | 4 | d | Hb |
|  | 7.02 | 4 | d | Ha |

$J_{ab}$ = 8 Hz
Note: There were only coupling constants of aromatic protons being reported

| Compound | δ in ppm | No of protons | Multiplicity | Assignment |
|---|---|---|---|---|
| 2-nonylphenol derivatives | 0.88 | 3 | t (b) | —CH$_3$ |
|  | 1.30 | 12 | m (b) | —(CH$_2$)$_6$— |
|  | 1.60 | 2 | m | Hf |
|  | 2.24 | 3 | s | Ar—CH$_3$ |
|  | 2.60 | 2 | t | He |
| Ha = CH$_3$ | 6.77 | 1 | t | Hc |
|  | 6.96 | 2 | d | Hb & Hd |
| $J_{bc}/J_{cd}$ = 8 Hz |  |  |  |  |
| Hb = CH$_3$ | 6.62 | 1 | d | Ha |
|  | 6.72 | 1 | dd | Hc |
|  | 7.02 | 1 | d | Hd |
| $J_{ac}$ = 2 Hz, $J_{cd}$ = 8 Hz |  |  |  |  |

TABLE 3-continued

¹H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|
| Hc = CH₃ | 6.67 | 1 | d | Ha |
|  | 6.89 | 1 | dd | Hb |
|  | 6.94 | 1 | d | Hd |
| $J_{ab}$ = 8 Hz, $J_{bd}$ = 2 Hz |  |  |  |  |
| Ha = Br | 6.72 | 1 | t | Hc |
|  | 7.04 | 1 | m | Hd |
|  | 7.28 | 1 | dd | Hb |
| $J_{bc}$ = 8 Hz, $J_{bd}$ = 2 Hz, $J_{cd}$ = 8 Hz, $J_{de}$ = 1 Hz |  |  |  |  |
| Hc = Br | 6.63 | 1 | d | Ha |
|  | 7.15 | 1 | dd | Hb |
|  | 7.22 | 1 | d | Hd |
| $J_{ab}$ = 8 Hz, $J_{bd}$ = 2 Hz |  |  |  |  |
| Ha = Hc = Br | 7.17 | 1 | m | Hd |
|  | 7.42 | 1 | d | Hb |
| $J_{bd}$ = 2 Hz, $J_{de}$ = 1 Hz |  |  |  |  |
| Ha = NO₂ | 6.89 | 1 | dd | Hc |
|  | 7.43 | 1 | m | Hd |
|  | 7.95 | 1 | dd | Hb |
| $J_{bc}$ = 8 Hz, $J_{bd}$ = 2 Hz, $J_{cd}$ = 8 Hz, $J_{de}$ = 1 Hz |  |  |  |  |
| Hc = NO₂ | 6.84 | 1 | d | Ha |
|  | 8.00 | 1 | dd | Hb |
|  | 8.06 | 1 | d | Hd |
| $J_{ab}$ = 8 Hz, $J_{bd}$ = 2 Hz |  |  |  |  |
| Ha = Br | 8.01 | 1 | d | Hd |
| Hc = NO₂ | 8.27 | 1 | d | Hb |
| Ha = NO₂ | 8.02 | 1 | d | Hd |
| Hc = Br | 8.27 | 1 | d | Hb |
| $J_{bd}$ = 2 Hz |  |  |  |  |
| Hb = OH | 6.31 | 1 | d | Ha |
| 4-nonyl- | 6.35 | 1 | dd | Hc |
| resorcinol | 6.94 | 1 | d | Hd |

$J_{ac}$ = 2 Hz, $J_{cd}$ = 8 Hz

*Structure: Resorcinol derivative with OH groups, $H_a$, $H_b$, $H_c$, $H_d$, $H_e$ labels on benzene ring with $-C(H_d)(H_e)-C(H_d)(H_e)-(CH_2)_9-CH_3$ chain*

| Compound | δ in ppm | No of protons | Multiplicity | Assignment |
|---|---|---|---|---|
| Resorcinol/coumarin derivatives | 0.88 | 3 | t (b) | —CH₃ |
|  | 1.26 | 18 | m (b) | —(CH₂)₉— |
|  | 1.56 | 2 | m | He |
|  | 2.58 | 2 | t | Hd |
| Ha = Br | 6.54 | 1 | d | Hb |
|  | 6.95 | 1 | d | Hc |
| $J_{bc}$ = 8 Hz |  |  |  |  |
| Hb = Br | 6.49 | 1 | s | Ha |
|  | 7.15 | 1 | s | Hc |
| Ha = Hb = Br | 7.18 | 1 | s | Hd |

*Structure: Coumarin derivative with CH₃, $H_a$, $H_b$, $H_c$, $H_d$, $H_e$ labels, OH group, and $-C(H_d)(H_e)-C(H_d)(H_e)-(CH_2)_9-CH_3$ chain*

| Compound | δ in ppm | No of protons | Multiplicity | Assignment |
|---|---|---|---|---|
| coumarin derivative | 2.42 | 3 | s | —CH₃ attached to double bond |
|  | 6.12 | 1 | s | Ha |
|  | 7.16 | 1 | s | Hc |
|  | 7.30 | 1 | s | Hb |

TABLE 3-continued $^1$H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|

Structure: bisphenol with —C(He)(Hf)—C(He)(Hf)—(CH$_2$)$_n$—C(Hf)(He)—C(Hf)(He)— linker; aromatic rings bear OH, Ha, Hb, Hc, Hd positions.

| Compound | δ in ppm | No of protons | Multiplicity | Assignment |
|---|---|---|---|---|
| n = 4 | 1.32 | 8 | m (b) | —(CH$_2$)$_4$— |
| n = 5 | 1.32 | 10 | m (b) | —(CH$_2$)$_5$— |
|  | 1.60 | 4 | m (b) | Hf |
|  | 2.60 | 4 | t | He |
|  | 6.75 | 2 | dd | Ha |
|  | 6.86 | 2 | td | Hc |
|  | 7.07 | 2 | dd | Hd |
|  | 7.10 | 2 | td | Hb |
| $J_{ab}$ = 8 Hz = $J_{bc}$ = $J_{cd}$, $J_{ac}$ = $J_{bd}$ = 2 Hz |  |  |  |  |
| n = 6 | 1.32 | 12 | m (b) | —(CH$_2$)$_2$— |
|  | 1.60 | 4 | m (b) | Hf |
|  | 2.30 | 6 | s | Ar—CH$_3$ |
|  | 2.60 | 4 | t | He |
| Ha = CH$_3$ | 6.88 | 2 | t | Hc |
|  | 7.07 | 4 | d | Hb & Hd |
| $J_{bc}/J_{cd}$ = 8 Hz |  |  |  |  |
| Hb = CH$_3$ | 6.60 | 2 | d | Ha |
|  | 6.70 | 2 | dd | Hc |
|  | 7.01 | 2 | d | Hd |
| $J_{ac}$ = 2 Hz, $J_{cd}$ = 8 Hz |  |  |  |  |
| Hc = CH$_3$ | 6.63 | 2 | d | Ha |
| Compounds | 6.86 | 2 | dd | Hb |
|  | 6.91 | 2 | d | Hd |

$J_{ab}$ = 8 Hz, $J_{bd}$ = 2 Hz

Structure: bis(resorcinol) analogue with —C(Hd)(He)—C(Hd)(He)—(CH$_2$)$_n$—C(He)(Hd)—C(He)(Hd)— linker; aromatic rings bear OH, HO, Ha, Hb, Hc, Hd.

| Compound | δ in ppm | No of protons | Multiplicity | Assignment |
|---|---|---|---|---|
| n = 4 | 1.23 | 8 | m (b) | —(CH$_2$)$_4$— |
| n = 6 | 1.23 | 12 | m (b) | —(CH$_2$)$_6$— |
| n = 7 | 1.23 | 14 | m (b) | —(CH$_2$)$_7$— |
| n = 8 | 1.23 | 16 | m (b) | —(CH$_2$)$_8$— |
|  | 1.53 | 4 | m | He |
|  | 2.26 | 4 | t | Hd |
|  | 6.05 | 2 | dd | Hb |
|  | 6.17 | 2 | d | Ha |
|  | 6.63 | 2 | d | Hc |
| $J_{ab}$ = 2 Hz, $J_{bc}$ = 8 Hz |  |  |  |  |
| n = 6 | $^1$H signals from methylene chain are similar to compound No 25 above |  |  |  |
| Ha = CH$_3$ | 2.14 | 6 | s | Ar—CH$_3$ |
|  | 6.38 | 2 | d | Hb |
|  | 6.75 | 2 | d | Hc |

$J_{bc}$ = 8 Hz

Structure: bis-aryl compound with R$_1$, R$_2$ substituents and —C(He)(Hf)—C(He)(Hf)—(CH$_2$)$_6$—C(Hf)(He)—C(Hf)(He)— linker.

$^1$H signals from methylene chain are similar to 25 above

| Compound | δ in ppm | No of protons | Multiplicity | Assignment |
|---|---|---|---|---|
| R$_1$ = OH | 6.64 | 4 | m | Ha & Hb |
| R$_2$ = Hb | 6.75 | 2 | dd | Hd |
|  | 7.13 | 2 | t | Hc |

TABLE 3-continued

¹H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|
| $J_{ab} = J_{bd} = 2$ Hz, $J_{bc} = J_{cd} = 8$ Hz | | | | |
| $R_1$ = OH | 2.20 | 6 | s | Ar—$CH_3$ |
| $R_2$ = $CH_3$ | 6.60 | 2 | d | Ha |
| | 6.67 | 2 | dd | Hd |
| | 7.01 | 2 | d | Hc |
| $R_1$ = $CH_3$ | 2.21 | 6 | s | Ar—$CH_3$ |
| $R_2$ = OH | 6.67 | 2 | d | Hc |
| | 6.87 | 2 | dd | Hd |
| | 6.92 | 2 | d | Ha |

$J_{cd} = 8$ Hz, $J_{ad} = 2$ Hz

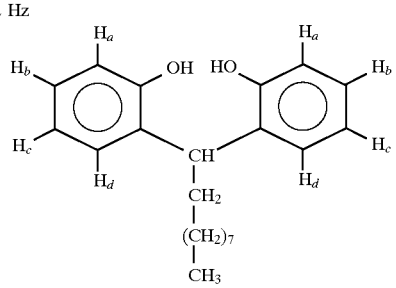

| | | | | |
|---|---|---|---|---|
| 1,1-bis- | 0.86 | 3 | t (b) | —$CH_3$ |
| (2-hydroxy- | 1.22 | 14 | m (b) | —$(CH_2)_7$— |
| phenyl)- | 2.12 | 2 | m | —$CH_2$— |
| decane | 4.47 | 1 | t | =(CH— |
| | 6.79 | 2 | dd | Ha |
| | 6.90 | 2 | td | Hc |
| | 7.03 | 2 | td | Hb |
| | 7.30 | 2 | dd | Hd |

$J_{ab} = J_{bc} = J_{cd} = 8$ Hz, $J_{ac} = 2$ Hz = $J_{bd}$

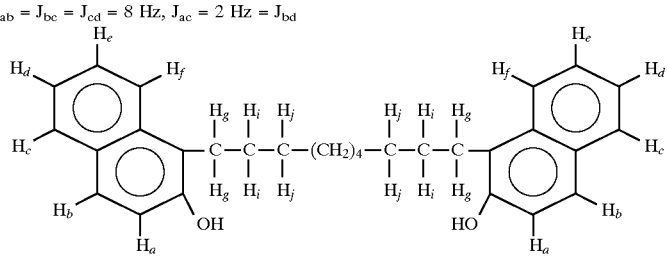

| | | | | |
|---|---|---|---|---|
| 1,10-bis(2- | 1.30 | 8 | m (b) | —$(CH_2)_4$— |
| hydroxy-1- | 1.46 | 4 | m (b) | Hj |
| naphthyl) | 1.65 | 4 | m (b) | Hi |
| decane | 3.01 | 4 | t | Hg |
| | 7.04 | 2 | d | Ha |
| | 7.31 | 2 | td | Hd |
| | 7.47 | 2 | td | He |
| | 7.61 | 2 | d | Hb |
| | 7.75 | 2 | dd | Hf |
| | 7.91 | 2 | dd | Hc |

$J_{ab} = 8$ Hz = $J_{cd} = J_{de} = J_{ef}$, $J_{ce} = J_{df} = 2$ Hz

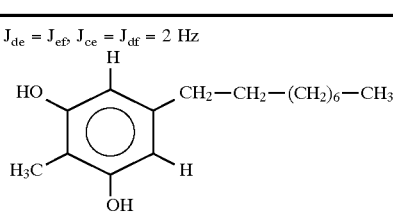

| | | | | |
|---|---|---|---|---|
| 3,5- | 0.88 | 3 | t (b) | —$CH_3$ |
| dihydroxy- | 1.26 | 12 | s (b) | —$(CH_2)_6$— |
| 4-methyl- | 1.55 | 2 | m | —$CH_2$— |
| phenyl- | 2.01 | 3 | s | Ar—$CH_3$ |
| nonane | 2.45 | 2 | t | Ar—$CH_2$— |

TABLE 3-continued $^1$H-NMR spectra of synthesised products
s: singlet, d: doublet, t: triplet, q: quintet, m: multiplet, b: broad

| Compound | δ in ppm | No of protons | Multiplicity | Assignment |
|---|---|---|---|---|
| | 6.24 | 2 | s | Ar—H |

[Structure: HO and H$_3$C substituted phenyl ring with H positions, connected via CH$_2$—CH$_2$—(CH$_2$)$_n$—CH$_2$—CH$_2$ to another phenyl ring with OH, CH$_3$, OH, H substituents]

| | | | | |
|---|---|---|---|---|
| n = 4 | 1.29 | 8 | m (b) | —(CH$_2$)$_4$— |
| n = 6 | 1.29 | 12 | m (b) | —(CH$_2$)$_6$— |
| n = 8 | 1.29 | 16 | m (b) | —(CH$_2$)$_8$— |
| n = 10 | 1.29 | 20 | m (b) | —(CH$_2$)$_{10}$— |
| | 1.53 | 4 | m | —CH$_2$— |
| | 2.04 | 6 | s | Ar—CH$_3$ |
| | 2.40 | 4 | t | Ar—CH$_3$ |
| | 6.24 | 4 | s | Ar—H |

Note: there are only coupling constants of aromatic proton.
*Summary of $^{13}$C-NMR (in δ ppm) spectra 2-nonylphenol derivatives
$^{13}$C-NMR of n-C$_9$H$_{19}$ chain. 14.19 (1C); 22.75 (1C); 29.41 (1C); 29.55 (1C); 29.58 (1C); 29.64 (2C); 30.86 (1C); 31.97 (1C);
Aromatic $^{13}$C-NMR of substituted phenols:
2-bromo-6-nonylphenol. 110.52 (1C); 121.30 (1C); 129.34 (1C); 129.63 (1C); 130.75 (1C); 150.1 (1C).
4-bromo-2-nonylphenol. 112.71 (1C); 116.83 (1C); 129.59 (1C); 131.07 (1C); 132.68 (1C); 150.09 (1C).
2,4-dibromo-6-nonylphenol. 110. (1C); 125.08 (1C); 125.52 (1C); 129.62 (1C); 132.1 (1C); 150.2 (1C).
2-nitro-6-nonylphenol. 119.31 (1C); 122.6 (1C); 132.37 (1C); 134.04 (1C); 137.41 (1C); 153.36 (1C).
4-nitro-2-nonylphenol. 115.19 (1C); 119.3 (1C); 123.54 (1C); 126.02 (1C); 130.73 (1C); 159.47 (1C).
4-bromo-2-nitro-6-nonylphenol. 109.92 (1C); 125.07 (1C); 125.51 (1C); 131.18 (1C); 141.26 (1C); 155.58 (1C).
4-dodecylresorcinol derivatives
$^{13}$C-NMR of n-C$_{12}$H$_{25}$ chain. 14.13 (1C); 22.7 (1C); 29.37 (1C); 29.41 (1C); 29.53 (1C); 29.62 (1C); 29.65 (1C); 29.68 (2C); 29.85 (1C); 30.17 (1C); 31.93 (1C).
Aromatic $^{13}$C-NMR of substituted resorcinols:
2-bromo-6-dodecylresorcinol. 99.63 (1C); 107.37 (1C); 122 (1C); 129.38 (1C); 150.24 (1C); 150.61 (1C).
4-bromo-6-dodecylresorcinol. 100.52 (1C); 103.17 (1C); 123 (1C); 132.17 (1C); 150.79 (1C); 154 (1C).
2,4-dibromo-6-dodecylresorcinol. 98.68 (1C); 99.62 (1C); 123.46 (1C); 131.1 (1C); 147.3 (1C); 150.52 (1C)
6-dodecyl-7-hydroxy-4-methylcoumarin
($^{13}$C-NMR of n-C$_{12}$H$_{25}$ are similar to those of resorcinol above)
Aromatic $^{13}$C. 102.62 (1C); 110.7 (1C); 112.37 (1C); 125 (1C); 127.28 (1C); 153.35 (1C); 159.12 (1C); 162.3 (1C).
1,11-bis(2,4-dihydroxyphenyl)undecane: 29.37 (2C); 29.41 (2C); 29.43 (3C); 29.46 (2C); 30.13 (2C); 102.93 (2C); 106.68 (2C); 120.50 (2C); 130.29 (2C); 155.24 (2C); 155.57 (2C).
1,2-bis(2,4-dihydroxyphenyl)dodecane: 28.91 (2C); 29.02 (2C); 29.05 (4C); 29.09 (2C); 29.69 (2C); 102.39 (2C); 105.79 (2C); 119.68 (2C); 129.54 (2C); 155.11 (2C); 155.45 (2C).
1,10-bis(2,4-dihydroxy-3-methylphenyl)decane: 8.51 (2C); 29.43 (2C); 29.47 (2C); 29.49 (2C); 29.86 (2C); 30.06 (2C); 107 (2C); 110.42 (2C); 119.76 (2C); 126.6 (2C); 152.65 (2C); 153.55 (2C).
1,10-bis(3-hydroxy-4-methylphenyl)decane: 15.31 (2C); 29.25 (2C); 29.46 (2C); 29.5 (2C); 31.41 (2C); 35.47 (2C); 114.92 (2C); 120.59 (2C); 120.76 (2C); 130.72 (2C); 142.31 (2C); 153.52 (2C).
2-methyl-5-nonylresorcinol: 7.73 (1C); 14.12 (1C); 22.69 (1C); 29.3 (1C); 29.35 (1C); 29.54 (1C); 31.21 (1C); 31.91 (1C); 107.31 (1C); 107.8 (2C); 142.05 (1C); 154.46 (2C).
1,8-bis(3,5-dihydroxy-4-methylphenyl)octane: 8.37 (2C); 29.93 (2C); 30.18 (2C); 32.11 (2C); 36.24 (2C); 107.34 (2C); 107.47 (4C); 141.59 (2C); 156.89 (4C).
1.10-bis(3,5-dihydroxy-4-methylphenyl)decane: 8.34 (2C); 29.94 (2C); 30.32 (4C); 32.13 (2C); 36.25 (2C); 107.34 (2C); 107.45 (4C); 141.59 (2C); 156.9 (4C).
1,12-bis(3,5-dihydroxy-4-methylphenyl)dodecane: 8.37 (2C); 29.97 (2C); 30.26 (2C); 30.34 (2C); 30.38 (2C); 32.15 (2C); 36.27 (2C); 107.34 (2C); 107.45 (4C); 141.58 (2C); 156.9 (4C).

TABLE 4

Chemical ionisation mass spectra of the synthesised alkylphenols and α,ω-bis (hydroxyphenyl)alkanes.

| m/e | intensity(%) | inference |
|---|---|---|
| Mass spectra of the intermediate products | | |
| 2-octanoylphenol | | |
| 261 | 4 | M + 41 |
| 249 | 11 | M + 29 |
| 221 | 100 | M + 1 |
| 127 | 6 | loss of phenol |
| 2-nonanoylphenol | | |
| 275 | 5 | M + 41 |
| 263 | 10 | M + 29 |

TABLE 4-continued

Chemical ionisation mass spectra of the synthesised alkylphenols and α,ω-bis(hydroxyphenyl)alkanes.

| | | |
|---|---|---|
| 235 | 100 | M + 1 |
| 141 | 9 | loss of phenol |
| 2-decanoylphenol | | |
| 289 | 5 | M + 41 |
| 277 | 16 | M + 29 |
| 249 | 100 | M + 1 |
| 155 | 15 | loss of phenol |
| 121 | 16 | 2-OH-benzoyl cation |
| 4-octanoylphenol | | |
| 221 | 100 | M + 1 |
| 127 | 13 | loss of phenol |
| 113 | 6 | loss of octane |
| 4-nonanoylphenol | | |
| 235 | 100 | M + 1 |
| 221 | 5 | loss of CH3 group |
| 141 | 6 | loss of phenol |
| 135 | 7 | loss of heptane |
| 4-decanoylphenol | | |
| 289 | 5 | M + 41 |
| 277 | 12 | M + 29 |
| 249 | 100 | M + 1 |
| 221 | 8 | loss of ethylene |
| 155 | 10 | loss of phenol |
| 135 | 8 | loss of octane |
| 3-benzyloxybenzaldehyde | | |
| 253 | 5 | M + 41 |
| 241 | 12 | M + 29 |
| 213 | 100 | M + 1 |
| 135 | 16 | loss of benzene |
| diphenyl decanedioate | | |
| 383 | 7 | M + 29 |
| 355 | 12 | M + 1 |
| 261 | 100 | loss of phenol |
| diphenyl dodecanedioate | | |
| 411 | 20 | M + 29 |
| 383 | 5 | M + 1 |
| 289 | 100 | loss of phenol |
| diphenyl tetradecanedioate | | |
| 439 | 15 | M + 29 |
| 411 | 4 | M + 1 |
| 317 | 100 | loss of phenol |
| 1,10-bis(2-hydroxyphenyl)-decane-1,10-dione | | |
| 383 | 6 | M + 29 |
| 355 | 100 | M + 1 |
| 261 | 10 | loss of phenol |
| 1,12-bis(2-hydroxyphenyl)-dodecane-1,12-dione | | |
| 423 | 8 | M + 41 |
| 411 | 20 | M + 29 |
| 383 | 100 | M + 1 |
| 289 | 5 | loss of phenol |
| 1,14-bis(2-hydroxyphenyl)-tetradecane-1,14-dione | | |
| 451 | 6 | M + 41 |
| 439 | 16 | M + 29 |
| 411 | 100 | M + 1 |
| 317 | 5 | loss of phenol |
| 1-(2-hydroxyphenyl)-10-(4-hydroxyphenyl)decane-1,10-dione | | |
| 383 | 8 | M + 29 |
| 355 | 100 | M + 1 |
| 327 | 10 | loss of 28 mass unit |
| 261 | 14 | loss of phenol |
| 135 | 25 | $C_6H_4(OH)COCH_2^+$ ion |
| 121 | 15 | $C_6H_4(OH)CO^+$ ion |
| 1-(2-hydroxyphenyl)-12-(4-hydroxyphenyl)dodecane-1,12-dione | | |
| 423 | 8 | M + 41 |
| 411 | 20 | M + 29 |
| 383 | 100 | M + 1 |
| 289 | 10 | loss of phenol |
| 121 | 5 | $C_6H_4(OH)CO^+$ ion |
| 1-(2-hydroxyphenyl)-14-(4-hydroxyphenyl)tetradecane-1,14-dione | | |
| 451 | 6 | M + 41 |
| 439 | 18 | M + 29 |
| 411 | 100 | M + 1 |
| 355 | 18 | loss of butene |
| 317 | 10 | loss of phenol |
| 1,10-bis(4-hydroxyphenyl)-decane-1,10-dione | | |
| 395 | 6 | M + 41 |
| 383 | 15 | M + 29 |
| 355 | 100 | M + 1 |
| 261 | 8 | loss of phenol |
| 121 | 15 | $C_6H_4(OH)CO^+$ ion |
| 1,12-bis(4-hydroxyphenyl)-dodecane-1,12-dione | | |
| 423 | 6 | M + 41 |
| 411 | 16 | M + 29 |
| 383 | 100 | M + 1 |
| 289 | 8 | loss of phenol |
| 137 | 18 | $C_6H_4(OH)C(OH)^+CH3$ |
| 123 | 12 | $C_6H_4(OH)C(OH)^+H$ |
| 1,14-bis(4-hydroxyphenyl)-tetradecane-1,14-dione | | |
| 451 | 5 | M + 41 |
| 439 | 18 | M + 29 |
| 411 | 100 | M + 1 |
| 317 | 8 | loss of phenol |
| 121 | 12 | 4-OH-benzoyl cation |

Mass spectra of alkylphenols and α,ω-bis(hydroxyphenyl)alkanes 2- and 4-octylphenols

| | | |
|---|---|---|
| 247 | 8 | M + 41 |
| 235 | 16 | M + 29 |
| 207 | 100 | M + 1 |
| 107 | 20 | $C_6H_4(OH)CH_2^+$ ion |

2-, 3- and 4-nonylphenols

| | | |
|---|---|---|
| 261 | 6 | M + 41 |
| 249 | 12 | M + 29 |
| 221 | 100 | M + 1 |
| 107 | 18 | $C_6H_4(OH)CH_2^+$ ion |

2- and 4-decylphenol

| | | |
|---|---|---|
| 275 | 5 | M + 41 |
| 263 | 16 | M + 29 |
| 235 | 100 | M + 1 |
| 107 | 16 | $C_6H_4(OH)CH_2^+$ ion |

1,10-bis(hydroxyphenyl)decanes and 1-(2-hydroxyphenyl)-10-(4-hydroxyphenyl)decane

| | | |
|---|---|---|
| 367 | 6 | M + 41 |
| 355 | 20 | M + 29 |
| 327 | 100 | M + 1 |
| 107 | 15 | $C_6H_4(OH)CH_2^+$ ion |

TABLE 4-continued

Chemical ionisation mass spectra of the synthesised alkylphenols and α,ω-bis(hydroxyphenyl)alkanes.

1,12-bis(hydroxyphenyl)-dodecanes and 1-(hydroxyphenyl)-12-(4-hydroxyphenyl)-dodecane

| m/e | INTENSITY (%) | INFERENCE |
|---|---|---|
| 395 | 5 | M + 41 |
| 383 | 20 | M + 29 |
| 355 | 100 | M + 1 |
| 107 | 6 | $C_6H_4(OH)CH_2^+$ ion |

1,14-bis(hydroxyphenyl)-tetradecanes and 1-(2-hydroxyphenyl)-14-(4-hydroxyphenyl)-tetradecane

| m/e | INTENSITY (%) | INFERENCE |
|---|---|---|
| 423 | 5 | M + 41 |
| 411 | 20 | M + 29 |
| 383 | 100 | M + 1 |
| 107 | 5 | $C_6H_4(OH)CH_2^+$ ion |

Note: The signals with intensity less than 5% were not accounted.

| m/e | INTENSITY (%) | INFERENCE |
|---|---|---|
| 2-,3- and 4-methyl-6-nonylphenol | | |
| 275 | 5 | M + 41 |
| 263 | 20 | M + 29 |
| 235 | 100 | M + 1 |
| 219 | 5 | loss of methane |
| 121 | 10–20 | loss of $C_8H_{18}$ |
| 2- and 4-bromo-6-nonylphenol | | |
| 327 | 10–20 | M + 29 |
| 299 | 100 | M + 1 |
| 185 | 15 | loss of $C_8H_{18}$ |
| 127 | 5–10 | $(C_9H_{19})^+$ |
| 2,4-dibromo-6-nonylphenol | | |
| 419 | 15 | M + 41 |
| 407 | 25 | M + 29 |
| 377 | 100 | M + 1 |
| 363 | 15 | loss of methane |
| 299 | 18 | loss of Br |
| 265 | 20 | loss of octane |
| 127 | 45 | $(C_9H_{19})^+$ |
| 2- and 4-nitro-6-nonylphenol | | |
| 306 | 5 | M + 41 |
| 294 | 15 | M + 29 |
| 266 | 100 | M + 1 |
| 250 | 5 | loss of methane |
| 236 | 10–12 | loss of ethane |
| 2-bromo-4-nitro-6-nonylphenol/ 4-bromo-2-nitro-6-nonylphenol | | |
| 372 | 12 | M + 29 |
| 344 | 100 | M + 1 |
| 314 | 10 | loss of ethane |
| 266 | 20 | loss of Br |
| 248 | 10 | loss of heptene |
| 4-nonylresorcinol | | |
| 277 | 8 | M + 41 |
| 265 | 20 | M + 29 |
| 237 | 100 | M + 1 |
| 123 | 30 | $(C_7H_7O_2)^+$ |
| 2- and 4-bromo-6-dodecyl-resorcinol | | |
| 385 | 15 | M + 29 |
| 357 | 100 | M + 1 |
| 279 | 10–20 | loss of Br |
| 201 | 15–25 | loss of $C_{11}H_{24}$ |

TABLE 4-continued

Chemical ionisation mass spectra of the synthesised alkylphenols and α,ω-bis(hydroxyphenyl)alkanes.

| m/e | INTENSITY (%) | INFERENCE |
|---|---|---|
| 135 | 5–10 | $(C_8H_7O_2)^+$ |
| 2,4-dibromo-6-dodecylresorcinol | | |
| 477 | 8 | M + 41 |
| 465 | 15 | M + 29 |
| 437 | 100 | M + 1 |
| 357 | 45 | loss of Br |
| 281 | 20 | loss of $C_{11}H_{24}$ |
| 201 | 10 | loss of 236 mass unit |
| 135 | 15 | $(C_8H_7O_2)^+$ |
| 6-dodecyl-7-hydroxy-4-methylcoumarin | | |
| 385 | 8 | M + 41 |
| 373 | 15 | M + 29 |
| 345 | 100 | M + 1 |
| 135 | 10 | $(C_8H_7O_2)^+$ |
| 1,8-bis(2-hydroxyphenyl)octane | | |
| 339 | 5 | M + 41 |
| 327 | 20 | M + 29 |
| 299 | 100 | M + 1 |
| 135 | 30 | $(C_9H_{11}O)^+$ |
| 1,9-bis(2-hydroxyphenyl)nonane | | |
| 353 | 6 | M + 41 |
| 341 | 20 | M + 29 |
| 313 | 100 | M + 1 |
| 1,10-bis[2-hydroxy-3(4- and 5-)methylphenyl]decanes | | |
| 395 | 5 | M + 41 |
| 383 | 20–25 | M + 29 |
| 355 | 100 | M + 1 |
| 1,8-bis(2,4-dihydroxyphenyl)-octane | | |
| 371 | 5 | M + 41 |
| 359 | 25 | M + 29 |
| 331 | 100 | M + 1 |
| 315 | 5 | loss of methane |
| 1,10-bis(2,4-dihydroxyphenyl)-decane | | |
| 399 | 5 | M + 41 |
| 387 | 20 | M + 29 |
| 359 | 100 | M + 1 |
| 1,11-bis(2,4-dihydroxyphenyl)-undecane | | |
| 413 | 10 | M + 41 |
| 401 | 30 | M + 29 |
| 373 | 100 | M + 1 |
| 123 | 5 | $(C_7H_7O_2)^+$ |
| 1,12-bis(2,4-dihydroxyphenyl)-dodecane | | |
| 427 | 5 | M + 41 |
| 415 | 30 | M + 29 |
| 387 | 100 | M + 1 |
| 1,10-bis(2,4-dihydroxy-3-methylphenyl)decane | | |
| 427 | 5 | M + 41 |
| 415 | 25 | M + 29 |
| 401 | 15 | M + 15 |
| 387 | 100 | M + 1 |
| 1,10-bis(3-hydroxyphenyl)-decane | | |
| 367 | 8 | M + 41 |
| 355 | 25 | M + 29 |
| 327 | 100 | M + 1 |
| 1,10-bis[3-hydroxy-4-methyl (and 4-hydroxy-3-methyl)- | | |

TABLE 4-continued

Chemical ionisation mass spectra of the synthesised alkylphenols and α,ω-bis (hydroxyphenyl)alkanes.

| phenyl]decanes | | |
|---|---|---|
| 395 | 5 | M + 41 |
| 383 | 20 | M + 29 |
| 355 | 100 | M + 1 |
| 1,1-bis(2-hydroxyphenyl)decane | | |
| 327 | 30 | M + 1 |
| 233 | 100 | loss of phenol |
| 135 | 20 | $(C_9H_{11}O)^+$ |
| 107 | 5 | $(C_7H_7O)^+$ |
| 1,10-bis(2-hydroxy-1-naphthyl)-decane | | |
| 467 | 5 | M + 41 |
| 455 | 15 | M + 29 |
| 427 | 70 | M + 1 |
| 135 | 50 | $(C_9H_{11}O)^+$ |
| 119 | 100 | |
| 2-methyl-5-nonylresorcinol | | |
| 291 | 5 | M + 41 |
| 279 | 20 | M + 29 |
| 251 | 100 | M + 1 |
| 235 | 8 | loss of methane |
| 135 | 8 | $(C_8H_7O_2)^+$ |
| 1,8-bis(3,5-dihydroxy-4-methyl-phenyl)octane | | |
| 399 | 8 | M + 41 |
| 387 | 25 | M + 29 |
| 359 | 100 | M + 1 |
| 135 | 5 | $(C_8H_7O_2)^+$ |
| 1,10-bis(3,5-dihydroxy-4-methylphenyl)decane | | |
| 427 | 5 | M + 41 |
| 415 | 20 | M + 29 |
| 387 | 100 | M + 1 |
| 135 | 5 | $(C_8H_7O_2)^+$ |
| 1,12-bis(3,5-dihydroxy-4-methylphenyl)dodecane | | |
| 455 | 5 | M + 41 |
| 443 | 25 | M + 29 |
| 415 | 100 | M + 1 |
| 1,14-bis(3,5-dihydroxy-4-methylphenyl)tetradecane (striatol) | | |
| 483 | 5 | M + 41 |
| 471 | 20 | M + 29 |
| 443 | 100 | M + 1 |
| 135 | 5 | $(C_8H_7O_2)^+$ |

Note: signals with intensity less than 5% were not accounted.

EXPERIMENTAL—NATURAL PRODUCTS
NOVEL RESORCINOLS FROM *GREVILLEA ROBUSTA* AND THEIR INHIBITORY ACTIVITY TO ERYTHROCYTE $Ca^{2+}$-ATPase General experimental procedures for extraction and isolation—The mobile phase was MeOH/$H_2O$ (82:18). Flow rate was 1.0 ml/min; Preparative HPLC were carried out with a Altex 100 solvent delivery system, equipped with Altex UV detector at 254 nm, a Activon Partisil ODS-3 column, 9×500 mm was used. The mobile phase was a gradient of MeOH/$H_2O$ (3:7) to MeOH in 60 min. or an isocratic mobile phase 65% $CH_3CN$ in $H_2O$, flow rate was 2.5 ml/min. 6251, 6252 were separated by these systems.

Plant Material—The stem of *Grevillea robusta* was collected in Sydney, Australia. A voucher specimen is available for inspection at the Department of Pharmacy, The University of Sydney. The stem wood, 5–10 cm in diameter, was sliced by an electrical plane and air dried.

Extraction and Isolation—A sample of 2 kg was extracted by percolation with $CHCl_3$/EtOH (1:1) for 3 days twice. After concentration of the extract in vacuo, the residue (20 g) was chromatographed by Silica gel short column vacuum chromatography collecting 250 ml fractions. The $Ca^{2+}$-ATPase assay gave an inhibitory activity of 50% at a concentration of 0.5 mg/ml. Fractions 1 to 4 (3.82 g) were eluted with petroleum/EtOAc (9:1–2:1). Fractions 7–9 (11.91 g), eluted from $CHCl_3$/MeOH(2:1), were inactive in the assay. They were not further studied. Fraction 5 (2.78 g), 6 (0.13 g), 6b(1.38 g) were eluted with $CHCl_3$/EtOAc(2:1), $CHCl_3$/MeOH (9:1), (8:2) respectively and gave strong inhibitory activity. Fraction 5 was further short column vacuum chromatographed with $CHCl_3$/EtOH (95:5) and gave grevillol (0.74 g). Fraction 6b was similarly chromatographed with $CH_2Cl_2$/EtOAc (4:1) to give 6b2 (37.4 mg). Fraction 6 was similarly separated into 10 fractions (each 50 ml) with petroleum /EtOAc (2:1), $CH_2Cl_2$/EtOAc (2:1), (1:1), (1:2), EtOAc, EtOAc/$CH_3CN$ (1:1). Only fraction 4–5 (63.4 mg) from $CH_2Cl_2$/EtOAc (2:1) gave strong inhibitory activity, 74% inhibition at 0.04 mg/ml. This fraction was then separated by gradient HPLC to give synapic aldehyde (623, 1.8 mg), and a nonpolar fraction 625 which was finally separated into 6251 (6.6 mg) and 6252 (1.3 mg) by preparative TLC, with $CHCl_3$/EtOH (95:5) as a solvent.

The methylation and ozonolysis is a method from Barrow R A, Capon R J (1991) Alkyl and alkenyl resorcinols from an Australian marine sponge, *Haliclona sp. Aust.J.Chem* 44 1393–1409. The sample to be methylated (2–8 mg) was stirred in acetone (3 ml) with $K_2CO_3$ (200 mg) and $CH_3I$ (0.5 ml) at room temperature for 20 h. The methylated products were isolated by preparative TLC with $CHCl_3$/EtOH (9.3:0.7) for 6b2, petroleum/EtOAc (8:2) for 6251, 6252. The methylated compounds (0.5–1 mg) in $CS_2$ (2 ml) at −78° C. were ozonolysed with a stream of $O_3$ and then triphenylphosphine (2 mg) added. The reaction mixtures were analysed directly by CI-MS.

The long chain resorcinols gave a characteristic purple colour on TLC after exposure to $I_2$ vapour and being left on the bench overnight, while resorcinol, resorcinylic acid, orcinol gave a dust brown colour.

Grebustol-A (6251)—Colourless oil; $R_f$ 0.51 ($CHCl_3$/ EtOH 9:1); $^1$H-NMR ($CDCl_3$, ppm) 1.26–1.35 (m, 12H, $CH_2$), 1.55 (m, 4H, $ArCH_2CH_2$), 2.00 (m, 4H, CH=CH$CH_2$), 2.10 (s, 3H, $ArCH_3$), 2.42–2.50 (m, 4H, $ArCH_2$), 4.70 (br.s., OH), 5.32–5.39 (m, 2H, CH=CH), 6.17(t, J=2.0 Hz, 1H, ArH), 6.24(br.s., 4H, ArH); $^{13}$C-NMR 156.5, 154.4, 142.6, 142.0, 130.0, 129.7, 108.1, 107.9, 100.2, 35.9, 35.6, 31.3, 31.1, 29.8, 29.7, 29.6, 29.4, 29.2, 29.1, 27.2, 7.9; CI-MS ($CH_4$) m/z 427{M+1}, 397, 285, 257, 229. 207; UV max(MeOH) 208.4 (logε 4.48), 274.4 (3.35), 279.4 (3.33).

Methylated Grebustol-A (6251 m)—$^1$H-NMR 1.26–1.38 (m, 12H, $CH_2$), 1.55 (m, 4H, $ArCH_2CH_2$), 2.00 (m, 4H, =CH$CH_2$), 2.06 (s, 3H, $ArCH_3$), 2.55 (m, 4H, $ArCH_2$), 3.78 (s, 6H, 2× $OCH_3$), 3.81 (s, 6H, 2× $OCH_3$), 5.32–5.41 (m, 2H, CH=CH), 6.29 (t, J=2.3 Hz, 1H, 2-H), 6.34 (d, J=2.3 Hz, 2H, 4, 6,-H), 6.36 (s, 2H, 4'6'-H); CI-MS {M+1}+ 483, EI-MS 482{M}$^+$ (32), 410(6), 386(13), 368(8), 353(3), 341(8), 149(12) 109(9); Ozonolysis of 6251 m, $^1$H-NMR 3.81, 3.78, 9.76, 9.77 (CHO), CI-MS 279, 237.

Norstriatol-B (6252)—colourless oil, $R_f$ 0.55 ($CHCl_3$/ EtOH 9:1); $^1$H-NMR($CDCl_3$, ppm) 1.25 (m, 12H, CH2), 1.58 (m, 4H, $CH_2$), 1.91 (m, 4H, =CH $CH_2$), 2.26 (m, 2H, 1-CH$_2$), 2.60 (m, 2H, 14-CH$_2$), 5.30 (m, 2H, CH=CH), 4.66 (br.s., OH), 6.45–6.49 (m, 4H, ArH); CI-MS 411{M+1}$^+$, 317, 285, 257; UV max (MeOH) 206.4 (log$\epsilon$ 4.61), 279.2 (3.49).

Methylated norstriatol-B (6252 m)- $^1$H-NMR 1.25 (m, 12H, CH$_2$), 1.54 (m, 4H, CH$_2$), 1.87 (m, 4H, CH=CHCH$_2$), 2.23 (m, 2H, 1-CH$_2$), 2.66 (m, 2H, 14-CH$_2$), 3.68 (d, J=3.0 Hz, 3H, 22-OCH$_3$), 3.69 (d, J=1.40 Hz, 6H, 17,19-OCH$_3$), 3.83 (d, J=1.45 Hz, 3H, 24-OCH$_3$), 5.30 (m, 2H, CH=CH), 6.42–6.45 (m, 4H, ArH); CI-MS 467 {m+1}$^+$; EI-MS 466 {m}$^+$(100), 451(2), 302(5), 149(10); $^{13}$C-NMR, 56.0, 56.1, 96.5, 104.8, 105.0;

Methylated striatol-B- $^{13}$C-NMR 56.0, 56.1, 96.5, 105.0, 130.3, 145.5.

Results and Discussion

Grebustol-A (6251)—Compound (II)

Grebustol-A (6251) (6.6 mg, 3.3ppm), molecular weight 426 (CI-MS), UV Max 274 nm, is different from striatol in having a double bond in the alkyl chain and a single benzyl methyl group as indicated by the $^1$H-NMR signals at 5.32–5.39 ppm (m, 2H), and 2.10 ppm (s, 3H). The mass spectrum and $^1$H-NMR spectrum of the methylated product revealed the presence of four OCH$_3$ groups (EI-MS 482), $^1$H-NMR 3.78 ppm (s, 6H) 3.81 (s, 6H)), $^1$H-NMR H-H COSY found the coupling of the signals 1.6–1.55, 1.26–2.00, 1.55–2.42, 2.00–5.35 ppm, but no coupling between the signals 1.55 and 2.00 ppm. This excludes the possibility of the double bond at C-10,11. $^1$H-NMR data indicated a non-symmetric structure. The CI-MS of ozonolysis products indicated aldehydes of molecular weight 278 and 236, consistent with a C-8,9 (m=7, n=5), or, C-9,10 (m=8, n=4) position for the double bond.

Norstriatol-B (6252)—Compound (III)

Norstriatol-B (6252) (1.3 mg, 0.65 ppm) is a desmethyl product of striatol-B. The CI-MS (CH$_4$ reagent gas) revealed a molecular weight 410. UV Max 279 nm. The $^1$H-NMR, UV, mass spectrum of norstriatol-B was consistent with the reported data for striatol-B [Ridley D D, et al (1970) Chemical studies of the Proteaceae IV *Aust.J.Chem.* 23, 147–183] and an authentic sample of striatol-B. It is a biphenyl derivative rather than a diphenyl ether derivative as with robustol [Cannon J R, et al (1973) Phenolic constituents of *Grevillea robusta* (Proteaceae). The structure of robustol, a novel macrocyclic phenol *Aust.J.Chem.* 26, 2257–2275]. The methylation of norstriatol-B gave tetramethyl norstriatol-B, which was identical to the substance formed by methylation of authentic striatol-B.

Table 1 shows that the inhibitory effect of grevillol to Ca$^{2+}$-ATPase was weak. The most potent compounds are striatol and grebustol-A, with IC$_{50}$ of 16 and 17 $\mu$M respectively. Without the benzylic methyl group, the activity was weaker, as in grebustol-B. Bisnorstriatol gave only 69.1% inhibition at the concentration of 500 $\mu$M. After the methylation of the phenolic hydroxy group, the activity of grebustol-B was lost. The inhibitory activity of striatol has been confirmed with purified erythrocyte Ca$^{2+}$-ATPase.

These results indicate the phenolic hydroxy groups were necessary for the inhibition to occur. The benzylic methyl group between the hydroxy groups enhances the activity. Also the double bond in the alkyl chain increased the inhibitory activity to Ca$^{2+}$-ATPase.

Erythrocyte membranes

Calmodulin-depleted erythrocyte membranes were prepared by continuous filtration through a hollow fibre, Ashahi plasma separator as described by W S Price, B D Roufogalis, P W Kuchel (1989), A simple and inexpensive method for preparing erythrocyte membranes by filtration through a hollow-filter system, *Anal. Biochem.*, 179, 190–193. Packed cells were obtained from the New South Wales Red Cross Transfusion Service, Sydney. The whole preparation was carried out at 4° C. 1 unit of packed red cells was washed 3 times with isotonic buffer, containing 130 mM KCl, 20 mM Tris-HCl (pH 7.4), and the cells were collected by centrifugation at 4,000 RPM. The cells were haemolysed by the buffer containing 1 mM EDTA, 10 mM Tris-Hcl (pH 7.4), 0.5 mM PMSF (phenylmethyl sulfonyl fluoride). The haemolyzate mixture was passed through the hollow fibre system until the membrane appeared white, and then washed with 10 mM potassium Hepes (pH 7.4). The membranes were collected by centrifugation at 10,000 RPM for 20 min, the membranes were resuspended in storage buffer containing 130 mM KCl, 2 mM dithiothreitol, 0.5 mM MgCl$_2$, 20 mM potassium-Hepes (pH 7.5). The membranes with protein concentration of 1.5–5.4 mg/ml were stored at –80° C. until required.

Ca$^{2+}$-ATPase assay

Erythrocyte membranes (0.071–0.098 mg/ml) were incubated at 37° C. for one hour in a total volume of 0.4 ml of 65 mM KCl, 20 mM potassium-Hepes, 5 mM MgCl$_2$, 50 $\mu$M CaCl$_2$, 0.1 $\mu$m calmodulin, 0.1 mM EGTA. The reaction was started by adding 2 mM ATP(pH 7.4). The phosphate liberated to the medium was determined spectrometrically according to the procedure of B U Raess, F F Vincenzi (1980), A semi-automated method for the determination of multiple membrane ATPase activities, *J.Pharmacological Methods* 4, 273–283. The activity of the Mg$^{2+}$-ATPase (assayed in the absence of added CaCl$_2$) was subtracted from the total activity assayed in the presence of Ca$^{2+}$. Phenols were dissolved in dimethyl sulfoxide (DMSO), the final concentration of DMSO in the assay mixture was 2.5%. DMSO itself had no effect on ATPase activities. A concentrated solution of the test substances was added to the reaction medium before adding ATP. Protein concentration was determined according to the method of O H Lowry, N J Rosebrough, A L Farr, R J Randall (1951) *J.Biol.Chem.* 193, 265–275; bovine serum albumin was used as a standard. The concentration of the free Ca$^{2+}$were calculated by computer using a program of D A Goldstein (1979) Calculation of the concentrations of free cations and cation-ligand complexes in solutions containing multiple divalent cations and ligands, *Biophys.J.*, 26, 235–242.

Control specific activity of the ATPases were (unit:nmoles/mg protein/min):Ca$^{2+}$-ATPase, was 25.8±4.0 (n=20), calmodulin stimulated Ca$^{2+}$-ATPase was 63.5±7.9 (n=16), while the Mg$^{2+}$-ATPase was 7.4±1.0 (n=20). The enzyme was inhibited by NAP-taurine by 60% at a concentration of 25 $\mu$M as shown by A Minocherhomjee, B D Roufogalis (1982), Selective antagonism of the Ca transport ATPase of the red cell membrane by N-(4-azido-2-nitrophenyl)-2-aminoethylsulfonate (NAP-taurine), *J.Biol.Chem.* 257, 5426–5430.

Ca$^{2+}$-ATPase assay (microplate method)

Erythrocyte membranes were incubated at 37° C. for one hour in a total volume of 60 $\mu$l of 65 mM KCl, 50 mM HEPES (pH=7.4), 5 mM MgCl$_2$, 50 $\mu$M CaCl$_2$, 0.1 mM EGTA and in absence and presence of calmodulin (0.3 $\mu$M). Test compounds were dissolved in dimethyl sulfoxide DMSO and 2 $\mu$l was added to the assay mixture prior the addition of ATP. The final concentration of DMSO in the assay mixture was 3%. The reaction was started by adding 2 mM ATP (pH=7.4). After 1 hour of incubation, colouring agent (180 $\mu$l) was added and incubated at 37° C. for 1/2 hrs.

The phosphate liberated to the assay medium was determined spectrometrically using a microplate reader at 750 nm. The activity of the $Mg^{2+}$-ATPase (assayed in the absence of added $CaCl_2$) was subtracted from the total activity assayed in the presence of $Ca^{2+}$. The results are shown in Table 1A.

ABBREVIATIONS

ATP: Adenosine triphosphate
ATPase: Adenosine triphosphatase
BHT: 2,6-di-tert-butyl-4-methylphenol
CI-MS: Chemical ionisation mass spectrometry
DMSO: Dimethyl sulfoxide
EI-MS: Electron impact mass spectrometry
EGTA: ethylenebis(oxyethylenenitrilo)tetraacetic acid
HEPES: 4-(2-hydroxyethyl)-1-piperazineethanesulfonic acid
HPLC: High-performance liquid chromatography
LDA: Lithium diisopropylamide
NAP: N-(4-azido-2-nitrophenyl)-2-aminoethanesulfonic acid
NMR: Nuclear magnetic resonance
PMSF: Phenylmethyl sulfonyl fluoride
SDS: Sodium dodecylsulfate
TLC: Thin layer chromatography

TOXICITY—BRINE SBRIMP ASSAY

The brine shrimp assay procedure determines $LC_{50}$ values of active compounds. Activities of a broad range of known active compounds are manifested as toxicity to brine shrimp (*Artemia salina* Leach). There are many applications of the assay including analysis of toxic substances, anaesthetics, morphine-like substances and cocarcinogenicity of phorbol esters. The assay shows good correlation with some cytotoxicities and its utility as a prescreen for some antitumour activities has been recently confirmed.

DMSO (dimethyl sulfoxide) was the solvent of choice because of its good solubilising properties and also because the phenolic substances used in the $Ca^{2+}$-ATPase inhibition study were already prepared with DMSO.

The method for testing solvent toxicity used was basically that reported by J L McLaughlin in *Methods of Plant Biochemistry* (1991), vol. 6 (K Hostettman, ed.), Academ Press, London, 1–32. DMSO solutions of the substances to be tested were added directly to the vials containing the brine shrimp. As the concentration of DMSO that we wished to use was higher than the recommended 1% v/v testing of the toxicity of the DMSO was therefore necessary. The concentrations of DMSO tested on the shrimp, along with the results from the assay which was done in duplicate are listed in Table 5.

TABLE 5

Concentrations of DMSO tested.

| Conc (% v/v) | % Deaths |
|---|---|
| 0 | 0 |
| 1 | 0 |
| 2 | 0 |
| 3 | 0 |
| 4 | 0 |
| 5 | 9 |
| 7 | 12 |
| 9 | 18 |
| 11 | 57 |

TABLE 5-continued

Concentrations of DMSO tested.

| Conc (% v/v) | % Deaths |
|---|---|
| 13 | 96 |
| 15 | 100 |
| 20 | 100 |
| 25 | 100 |

No toxicity towards brine shrimp was observed in a 24 hour period for concentrations of DMSO in brine up to 4% v/v.

Bioassay

Brine shrimp toxicity was assayed, except for some minor modifications, according to the method of McLaughlin et al as reported in Brine Shrimp: A convenient general bioassay for active plant constituents, B N Meyer, N R Ferrigni, J E Putman, L B Jacobsen, D E Nhols and J L McLaughlin. *Planta Medica* (1982), 45, 31–34 and Crown gall tumours on potato discs and brine shrimp lethality: Two simple bioassay for higher plant screening and fractionation. J L McLaughlin. *Methods of Plant Biochemistry* (1991), vol. 6 (K Hostettman, ed.), Academ Press, London, 1–32. Ten shrimp were added transferred to each of the vials and the volume adjusted to 4.9 mL. Each dose was performed in triplicate, including the control. In quick succession, the appropriate volume of additional DMSO for each dose, required to achieve a final concentration of 2%, was added before the appropriate volume of test solution. The vials were gently mixed and the time noted. After 24 hours, the number of survivors were counted and % mortality was determined. The test compounds were assayed at concentrations of 100 μM, 25 μM, 5 μM, 1 μM and 0.2 μM (and where appropriate concentrations of 0.04 μM and 0.008 μM).

The brine shrimp were able to survive without food in the vials over the 24 hour period and were therefore not fed.

The dose-response curves were constructed using the Sigmaplot computer program and the $LC_{50}$ value was calculated from the intersection point of the curve and the 50% mortality line. The $LC_{50}$ values were expressed in both μM and μg/mL.

TABLE 6

$LC_{50}$ values from brine shrimp bioassay

| MWt | Compound | $LC_{50}$ μM | μg/mL |
|---|---|---|---|
| 206 | 2-octylphenol | 1.5 | 0.31 |
| 220 | 2-nonylphenol | 0.48 | 0.11 |
| 234 | 2-decylphenol | 0.68 | 0.16 |
| 220 | 3-nonylphenol | 0.32 | 0.070 |
| 220 | 4-nonylphenol | 0.40 | 0.088 |
| 234 | 4-decylphenol | 0.27 | 0.064 |
| 234 | 2-nonanoylphenol | 0.63 | 0.15 |
| 234 | 4-nonanoylphenol | 0.10 | 0.024 |
| 176 | 2-cyclohexylphenol | >25 | >4.4 |
| 176 | 4-cyclohexylphenol | >25 | >4.4 |
| 298 | 1,8-bis(2-hydroxyphenyl)octane | 3 | 0.89 |
| 326 | 1,10-bis(2-hydroxyphenyl)decane | 1.9 | 0.62 |
| 326 | 1,10-bis(3-hydroxyphenyl)decane | 3 | 0.98 |
| 326 | 1,1-bis(2-hydroxyphenyl)decane | 14 | 4.6 |
| 354 | 1,10-bis(2-hydroxy-4- | 14 | 5 |

TABLE 6-continued

LC$_{50}$ values from brine shrimp bioassay

| MWt | Compound | LC$_{50}$ $\mu$M | LC$_{50}$ $\mu$g/mL |
|---|---|---|---|
| | methylphenyl)decane | | |
| 354 | 1,10-bis(2-hydroxy-3-methylphenyl)decane | 5.8 | 2.1 |
| 354 | 1,10-bis(3-hydroxy-4-methylphenyl)decane | 11 | 3.9 |
| 354 | 1,10-bis(4-hydroxy-3-methylphenyl)decane | 4.2 | 1.5 |
| 354 | 1-(2-hydroxy-3-methylphenyl)-10-(4-hydroxy-3-methylphenyl)decane | 2.2 | 0.78 |
| 354 | 1,12-bis(2-hydroxyphenyl)dodecane | 2.6 | 0.94 |
| 382 | 1,14-bis(2-hydroxyphenyl)tetradecane | 1.9 | 0.72 |
| 326 | 1,10-bis(4-hydroxyphenyl)decane | 0.81 | 0.26 |
| 354 | 1,12-bis(4-hydroxyphenyl)dodecane | 3.8 | 1.4 |
| 382 | 1,14-bis(4-hydroxyphenyl)tetradecane | 7.9 | 3.7 |
| 326 | 1-(2-hydroxyphenyl)-10-(4-hydroxyphenyl)decane | 0.35 | 0.11 |
| 354 | 1-(2-hydroxyphenyl)-12-(4-hydroxyphenyl)dodecane | 0.054 | 0.019 |
| 382 | 1-(2-hydroxyphenyl)-14-(4-hydroxyphenyl)tetradecane | 3.7 | 1.4 |
| 426 | 1,10-bis(2-hydroxy-1-naphthyl)decane | >25 | >11 |
| 358 | 1,8-bis(3,5-dihydroxy-4-methylphenyl)octane | >25 | >9 |
| 386 | 1,10-bis(3,5-dihydroxy-4-methylphenyl)decane | >25 | >9.7 |
| 414 | 1,12-bis(3,5-dihydroxy-4-methylphenyl)dodecane | >25 | >10 |
| 442 | 1,14-bis(3,5-dihydroxy-4-methylphenyl)tetradecane (striatol) | 11 | 4.9 |
| 414 | 1,14-bis(3,5-dihydroxyphenyl)-tetradecane (bisnorstriatol) | 40 | 17 |
| 330 | 1,8-bis(2,4-dihydroxyphenyl)octane | 74 | 24 |
| 358 | 1,10-bis(2,4-dihydroxyphenyl)decane | 37 | 13 |
| 372 | 1,11-bis(2,4-dihydroxyphenyl)undecane | >25 | >9.3 |
| 386 | 1,12-bis(2,4-dihydroxyphenyl)dodecane | 14 | 5.4 |
| 386 | 1,10-bis(2,4-dihydroxy-3-methylphenyl)decane | >25 | >9.7 |
| 194 | 4-hexylresorcinol | 62 | 12 |
| 236 | 4-nonylresorcinol | 10 | 2.4 |
| 278 | 4-dodecylresorcinol | 8.8 | 2.4 |
| 180 | 5-pentylresorcinol (olivetol) | >100 | >18 |
| 236 | 5-nonylresorcinol | >100 | >18 |
| 250 | 2-methyl-5-nonylresorcinol | 8.3 | 2.1 |
| 274 | 5-decylresorcinol | 54 | 15 |
| 292 | 5-tridecylresorcinol (grevillol) | 2.8 | 0.80 |
| 348 | 5-heptadecylresorcinol | >100 | >18 |
| 308 | ethyl 2,4-dihydroxy-6-nonylbenzoate | 2.6 | 0.8 |
| 466 | ethyl 3,5-dibromo-2,4-dihydroxy-6-nonylbenzoate | 0.78 | 0.36 |
| 322 | ethyl 2,4-dihydroxy-6-decylbenzoate | 2.3 | 0.75 |
| 480 | ethyl 3,5-dibromo-2,4-dihydroxy-6-decylbenzoate | 0.78 | 0.37 |
| 324 | 6-dodecyl-7-hydroxy-4-methylcoumarin | >25 | >8.1 |
| 328 | grifolin | 2.3 | 0.75 |
| 328 | neogrifolin | 28 | 9.0 |
| 424 | 5,7,2',6'-tetrahydroxy-8-lavandulylflavanone | >100 | >42 |
| 414 | podophyllotoxin | 3.8 (5.8) | 1.6* (2.4) |
| solvent: dimethyl sulfoxide (DMSO) | | | 11% v/v |

*LC$_{50}$ determined by Meyer et al. Planta medica (1982), 45, 31–34

DISCUSSION

In this bioassay, the estimated LC$_{50}$ value of the test compound indicates its toxicity to brine shrimp. A more useful comparison of potencies can be obtained by looking at the $\mu$M instead of $\mu$g/mL concentrations in Table 6.

Simple alkylphenols were very toxic with certain alkyl chain lengths. The most active of the alkylphenols measured was 4-decylphenol (LC$_{50}$=0.27 $\mu$M) compared with the most active of all compounds measured 1-(2-hydroxyphenol)-12-(4-hydroxyphenol)dodecane (LC$_{50}$=0.054 $\mu$M). Ketophenols were found to be more toxic than simple alkylphenols e.g. 4-nonanoylphenol (LC$_{50}$=0.10 $\mu$M). 4- and 5-Alkylresorcinols showed low toxicity except for 5-tridecylresorcinol (grevillol) (LC$_{50}$=2.8 $\mu$M) which was moderately toxic. The α,ω-bishydroxyphenylalkanes, for example 1,10-bis(2-hydroxyphenyl)decane (LC$_{50}$=1.9 $\mu$M), were moderately toxic. 1,10-Bis(2-hydroxy-4-methylphenyl)decane (LC$_{50}$=14 $\mu$M) and other substances with methyl groups on the phenyl groups showed reduced toxicity. The α,ω-bisresorcinylalkanes, including, striatol (LC$_{50}$=11 $\mu$M), bisnorstriatol (LC$_{50}$=40 $\mu$M) and 1,10-bis (2,4-dihydroxyphenyl)decane (LC$_{50}$=37 $\mu$M) showed relatively low toxicity.

A significant difference in toxicity exists between grifolin and neogrifolin (LC$_{50}$=2.3 $\mu$M and LC$_{50}$=28 $\mu$M respectively). Neogrifolin appears to be about ten-fold weaker than grifolin. Ca$^{2+}$-ATPase inhibition by these two compounds, on the other hand, was relatively strong and identical (grifolin's IC$_{50}$ was 22.5 $\mu$M while neogrifolin's IC$_{50}$ was 23.3 $\mu$M).

Podophyllotoxin was tested in order to check whether the bioassay's results were comparable with those of Meyer et al. The LC$_{50}$ from this study was 3.8 $\mu$M and is reasonably close to the LC$_{50}$ value of 5.8 $\mu$M determined by Meyer et al.

We claim:

1. Compounds of formula (III)

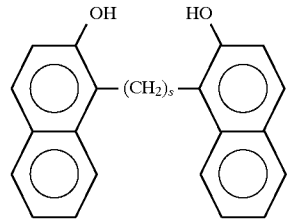

where s=8-16 or pharmaceutically acceptable derivatives thereof.

2. A method of preparing compounds of formula (III) as defined in claim 1 which comprises:

(i) treating the corresponding diacid with a suitable agent to provide the acid dichloride;

(ii) treating the corresponding acid dichloride with 2-naphthol followed by;

(iii) rearrangement of the diacyl groups; and (iv) followed by reduction of the acyl groups to provide compounds of formula (III).

3. A method for inhibiting in a subject the action of plasma membrane Ca$^{2+}$-ATPase enzymes relating to cardiovascular actions which comprises administering to the subject a compound of formula (III) as defined in claim 1.

4. A method of treatment or prophylaxis of cardiovascular disease related to the action of plasma membrane Ca$^{2+}$-ATPase enzyme in a subject which comprises administering to the subject a compound of formula (III) as defined in claim 1.

5. A pharmaceutical formulation comprising a compound of formula (III) as defined in claim 1, or pharmaceutically acceptable derivatives thereof in a pharmaceutically acceptable carrier.

* * * * *